United States Patent
Lin

(10) Patent No.: US 6,815,093 B2
(45) Date of Patent: Nov. 9, 2004

(54) LIGHT EMITTING MATERIALS BASED ON INDOLE SKELETON

(75) Inventor: Tung-Shen Lin, Tainan (TW)

(73) Assignee: Lightronik Technology, Inc. (TW)

( * ) Notice: Subject to any disclaimer, the term of this patent is extended or adjusted under 35 U.S.C. 154(b) by 73 days.

(21) Appl. No.: 10/341,426

(22) Filed: Jan. 14, 2003

(65) Prior Publication Data

US 2004/0137262 A1 Jul. 15, 2004

(51) Int. Cl.$^7$ ................ H05B 33/14; C07D 209/04; C09K 11/06

(52) U.S. Cl. ............. 428/690; 428/917; 313/504; 313/506; 548/455; 548/465; 548/467; 548/469

(58) Field of Search ................. 428/690, 917; 313/504, 506; 548/455, 465, 467, 469

(56) References Cited

U.S. PATENT DOCUMENTS

| | | |
|---|---|---|
| 3,935,031 A | 1/1976 | Adler |
| 4,127,412 A | 11/1978 | Rule et al. |
| 4,356,429 A | 10/1982 | Tang ..................... 313/583 |
| 4,769,292 A | 9/1988 | Tang et al. ............ 428/690 |
| 6,074,734 A | 6/2000 | Kawamura et al. .... 428/220 |
| 6,093,864 A | 7/2000 | Tokailin et al. ........ 528/25 |

*Primary Examiner*—Marie Yamnitzky
(74) *Attorney, Agent, or Firm*—Arent Fox, PLLC

(57) ABSTRACT

An indole-based compound represented by Formula (1) disclosed herein is useful in forming a light emitting material for an organic electroluminescent device. The organic electroluminescent device has a multi-layered structure comprising a cathode, an anode and at least one organic layer, wherein the at least one organic layer comprises the indole-based compound. The indole-based compound contains two light-emitting units, each having an indole-based structure, linked with a connecting unit, which is an arylamine. The color of the light emitted by the light emitting material can be adjusted by changing the connecting unit.

48 Claims, 8 Drawing Sheets

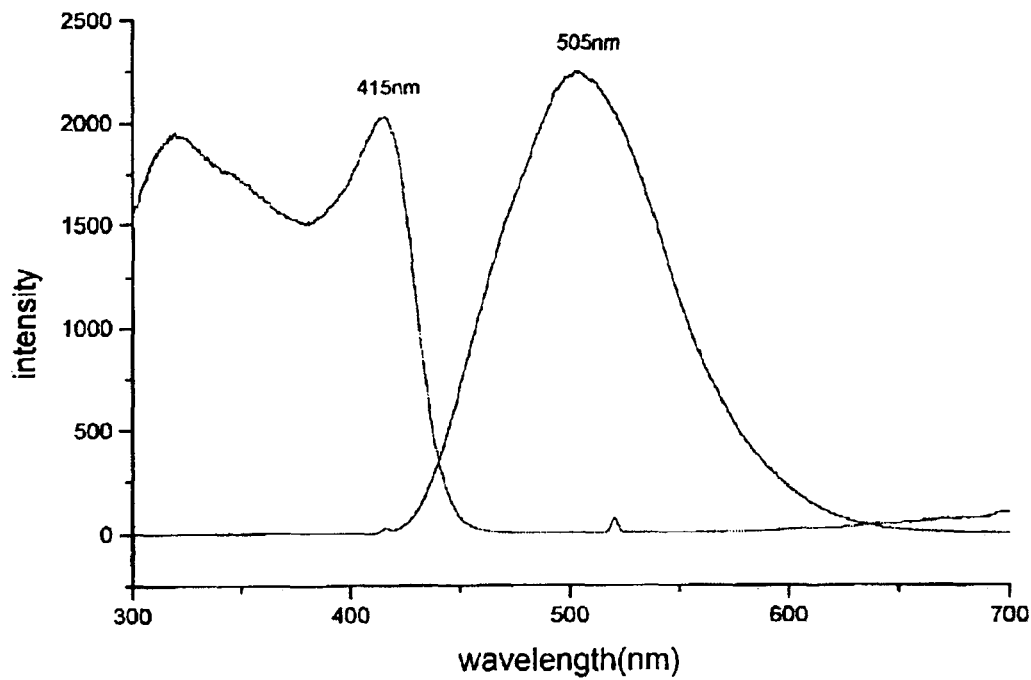
Fig. 4 (Excitation and Emission spectrum of A)
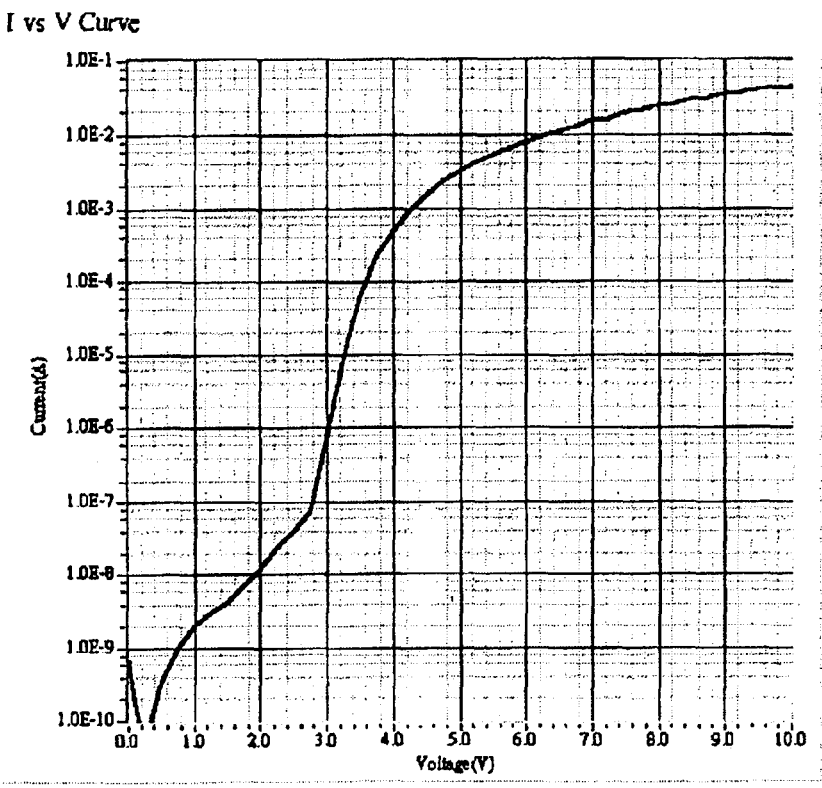
Fig. 5

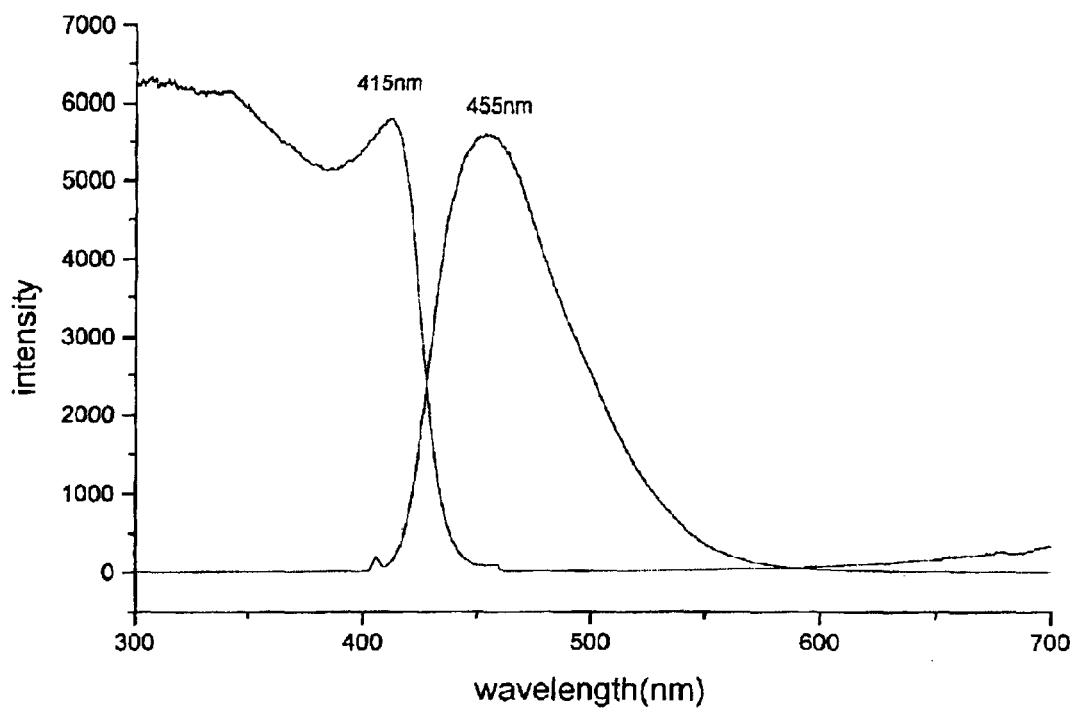
Fig. 9 (Excitation and Emission spectrum of B)
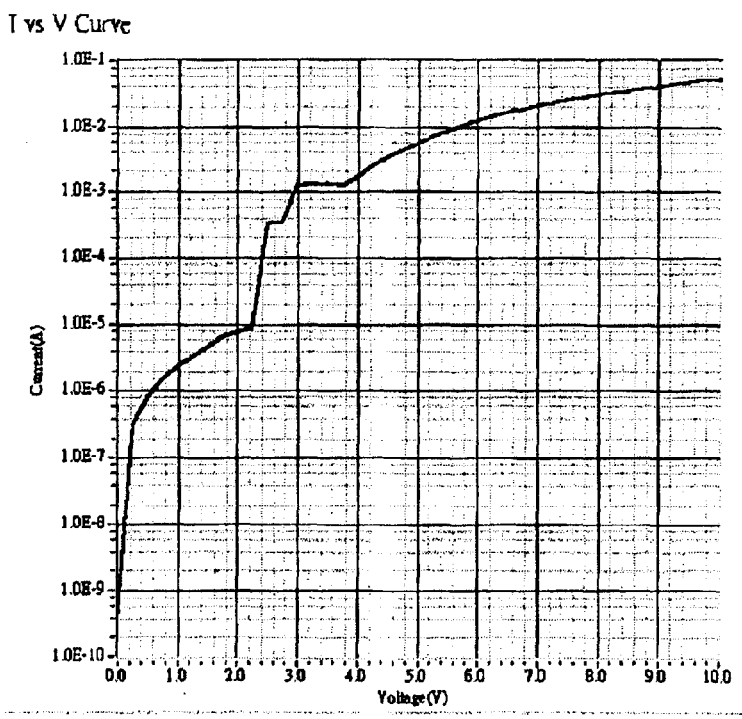
Fig. 10

LIGHT EMITTING MATERIALS BASED ON INDOLE SKELETON

BACKGROUND OF THE INVENTION

This invention generally relates to a light emitting device, and more specifically to an organic electroluminescent device containing a light emitting material having an indole skeleton and good light-emitting properties.

Organic electroluminescent devices (organic EL devices) are light emitting devices containing a fluorescent material which emits light in response to the recombination of holes and electrons injected from the anode and cathode (C. W. Tang et al. Applied Physics Letters, 1987, 51:913). The luminescence efficiency of organic EL devices can be improved by doping with a fluorescent dye. For instance, doping with a coumarin dye can greatly improve the luminescence efficiency of an organic EL device (Applied Physics letters, 1989, 65:3610). A well-known coumarin dye is C-545T (U.S. Pat. No. 4,769,292), which has the following structure:

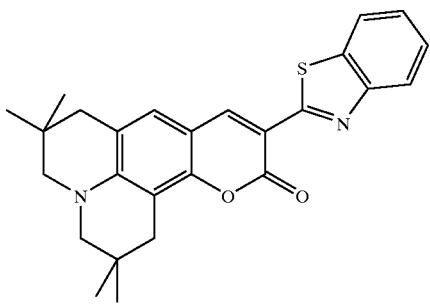

For improving the recombination efficiency of the injected holes and electrons, multi-layered devices have been introduced. A hole transporting layer (HTL) containing a hole transporting material (HTM) is used to improve hole injections and transporting from the anode into an organic layer. An example of a well-known HTM is NPB (4,4'-bis [N-(1-naphthyl)-N-phenyl-amino-]bisphenyl), which has the following structure:

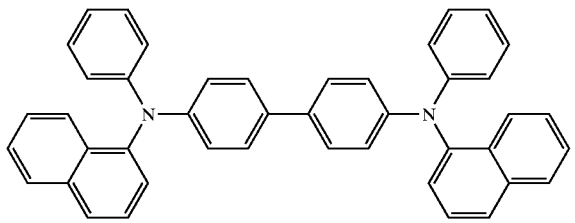

An electron transporting layer (ETL) containing an electron transporting material (ETM) is used to improve the electron injection from the cathode into the organic layer. A typical ETM, $Alq_3$ (aluminum tris (8-hydroxyquinolate)), has the following structure:

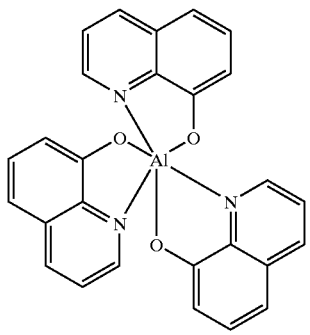

Other materials, such as oxadiazole compounds, triazine compounds, and triazole compounds, can also be used as ETMs.

Aromatic dimethylidyne compounds have been used as blue light emissive materials for organic EL devices (U.S. Pat. No. 6,093,864). An example of aromatic dimethylidyne compounds is (1,4-bis 2,2-di-phenylvinyl)biphenyl (DPVBi) having an EL peak at about 485 nm and the following structure:

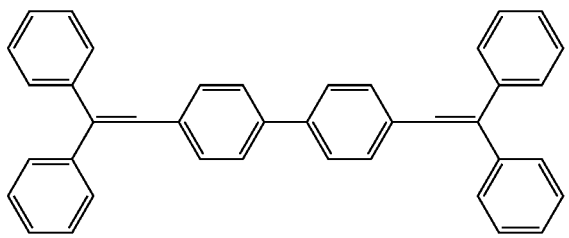

SUMMARY OF THE INVENTION

One of the objects of the present invention is to provide a new light emitting material based on an indole skeleton and another object is to provide an organic EL device which has good light emitting properties containing the new light emitting material. The organic EL device comprises an anode, cathode, and one or more organic thin film layers which contain one or more indole-based compounds represented by Formula (1):

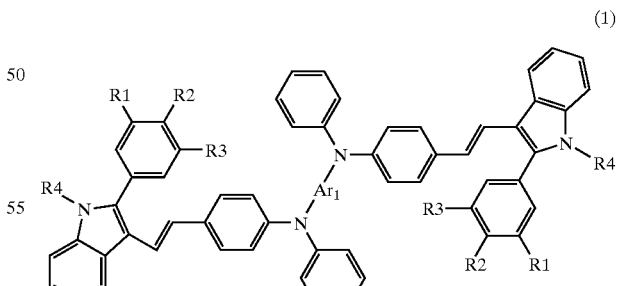

(1)

wherein $Ar_1$ represents a substituted or unsubstituted aromatic hydrocarbon group, a group formed by two aromatic hydrocarbon groups directly linked together, wherein the two aromatic hydrocarbon groups are independently substituted or unsubstituted, a substituted or unsubstituted aromatic heterocyclic group, a group formed by two aromatic heterocyclic groups directly linked together, wherein the two aromatic heterocyclic groups are independently substituted or unsubstituted, or a group formed by an optionally substituted aromatic hydrocarbon group directly linked with an optionally substituted aromatic heterocyclic group; R1, R2 and R3 each independently represents a H atom, F atom, CN group, substituted or unsubstituted alkyl group, substituted or unsubstituted aromatic hydrocarbon group, or substituted or unsubstituted amino group; any two of R1, R2 and R3 together with the attached carbon atoms may form an aromatic heterocyclic or hydrocarbon ring; and R4 represents a substituted or unsubstituted alkyl group, substituted or unsubstituted aromatic hydrocarbon group, or substituted or unsubstituted aromatic heterocyclic group. Within the scope of the invention are the indole-based compounds represented by Formula (1).

BRIEF DESCRIPTION OF THE INVENTION

FIG. 4 illustrates the thin film PL spectrum of Compound (A);

FIG. 5 illustrates the IV curve of Device Example 1 disclosed below;

FIG. 9 illustrates the thin film PL spectrum of Compound (B);

FIG. 10 illustrates the IV curve of Device Example 2 disclosed below;

DETAILED DESCRIPTION OF THE INVENTION

Figure 1:
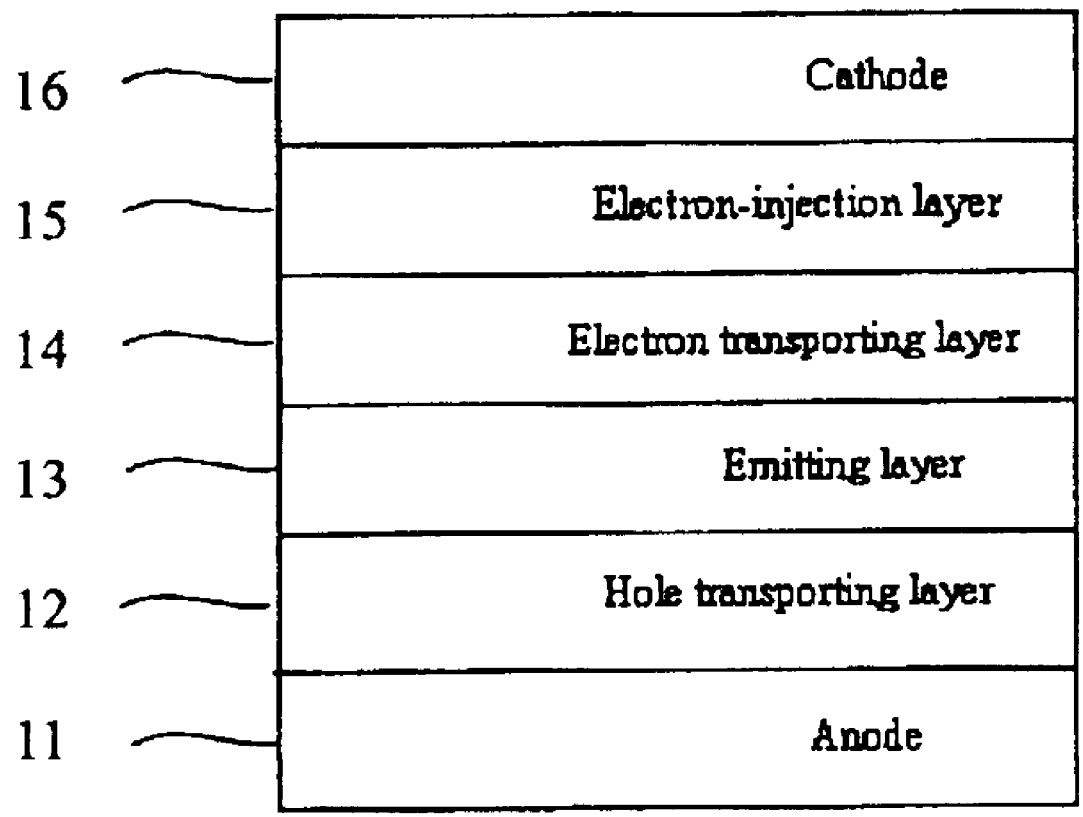
FIG. 1 is an schematic illustration of an organic EL device of the present invention.

The present invention provides an organic EL element comprising a light emitting material having an indole skeleton represented by Formula (1):

(1)

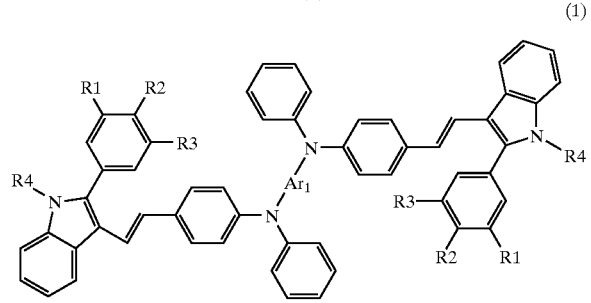

wherein $Ar_1$ represents a substituted or unsubstituted aromatic hydrocarbon group, a group formed by two aromatic hydrocarbon groups directly linked together, wherein the two aromatic hydrocarbon groups are independently substituted or unsubstituted, a substituted or unsubstituted aromatic heterocyclic group, a group formed by two aromatic heterocyclic groups directly linked together, wherein the two aromatic heterocyclic groups are independently substituted or unsubstituted, or a group formed by an optionally substituted aromatic hydrocarbon group directly linked with an optionally substituted aromatic heterocyclic group; R1, R2 and R3 each independently represents a H atom, F atom, CN group, substituted or unsubstituted alkyl group, substituted or unsubstituted aromatic hydrocarbon group, or substituted or unsubstituted amino group; any two of R1, R2 and R3 together with the attached carbon atoms may form an aromatic heterocyclic or hydrocarbon ring; and R4 represents a substituted or unsubstituted alkyl group, substituted or unsubstituted aromatic hydrocarbon group, or substituted or unsubstituted aromatic heterocyclic group.

Preferably, in Formula (1), $Ar_1$ represents a substituted or unsubstituted aromatic hydrocarbon group, a group formed by two identical aromatic hydrocarbon groups directly linked together, wherein the two aromatic hydrocarbon groups are substituted or unsubstituted, a substituted or unsubstituted aromatic heterocyclic group, or a group formed by two identical aromatic heterocyclic groups directly linked together, wherein the two aromatic heterocyclic groups are substituted or unsubstituted.

More preferably, $Ar_1$ represents an unsubstituted aromatic hydrocarbon group (e.g. phenylene and naphthalenediyl), a group formed by two identical unsubstituted aromatic hydrocarbon groups directly linked together (e.g. biphenyldiyl and binaphthyldiyl), an unsubstituted aromatic heterocyclic group (e.g. pyridiyl and pyrrolediyl), or a group formed by two identical unsubstituted aromatic heterocyclic groups directly linked together (e.g. bipyridydiyl and bipyrrolyldiyl).

Even more preferably, $Ar_1$ represents the unsubstituted aromatic hydrocarbon group or the group formed by two identical unsubstituted aromatic hydrocarbon groups directly linked together.

Much more preferably, $Ar_1$ represents phenylene (e.g. 1,3-phenylene and 1,4-phenylene), naphthalenediyl (e.g. 1,5-naphthalenediyl and 2,6-naphthalenediyl), antracenediyl (e.g. 9,10-anthracenediyl and 1,5-anthracenediyl) or biphenyldiyl (e.g. 4,4'-biphenyldiyl).

Even much more preferably, $Ar_1$ represents 1,4-phenylene, 1,5-naphthalenediyl 9,10-anthracenediyl or 4,4'-biphenyldiyl.

Most preferably, $Ar_1$ represents 1,4-phenylene or 4,4'-biphenyldiyl.

In Formula (1), preferably, R1, R2 and R3 each independently represents a H atom, an unsubstituted alkyl group, an unsubstituted aromatic hydrocarbon group, or a substituted or unsubstituted amino group; and two of R1, R2 and R3 do not form an aromatic heterocyclic or hydrocarbon ring.

More preferably, R1, R2 and R3 each independently represents a H atom, an unsubstituted alkyl group, or a substituted or unsubsituted amino group.

Even more preferably, R1, R2 and R3 each independently represents a H atom or substituted amino group (e.g. piperidinyl, piperazinyl, morpholinyl and thiomorpholinyl attached via a ring nitrogen atom).

Much more preferably, R1, R2 and R3 each represents a H atom, or R1 and R3 both resent a H atom and R2 represents 1-piperidinyl.

Most preferably, R1, R2 and R3 each represents a H atom.

In Formula (1), preferably, R4 represents an unsubstituted alkyl group, unsubstituted aromatic hydrocarbon group or unsubstituted aromatic heterocyclic group.

More preferably, R4 represents a $(C_1-C_6)$alkyl, phenyl, naphthyl or pyridinyl group.

Even more preferably, R4 represents a methyl or phenyl group.

Most preferably, R4 represents a phenyl group.

In this application, the term "aromatic hydrocarbon group" means an aromatic cyclic hydrocarbyl group. Examples of "aromatic hydrocarbon group" are phenyl, naphthyl, anthracenyl and phenanthrenyl groups. "Substituted" aromatic hydrocarbon group, used herein, refers to an aromatic hydrocarbon group substituted by one or more halogen atoms or OH, SH, ($C_1$–$C_6$)alkyl, ($C_2$–$C_6$)alkenyl, ($C_4$–$C_8$)cycloalkyl, ($C_{1-C6}$)alkoxy, ($C_{1-C6}$)alkylthio, trifluoromethyl, cyano, nitro, amino, mono-($C_1$–$C_6$)alkyl-amino, di-($C_1$–$C_6$)alkyl-amino, ($C_1$–$C_6$)alkyl-carbonyl, ($C_1$–$C_6$)alkoxy-carbonyl or carboxyl groups.

The term, "aromatic heterocyclic group", used herein refers to a 5- or 6-membered aromatic ring containing one to three N, S and/or O ring atoms with the remaining ring atoms being C optionally fused with a benzene or 5- or 6-membered aromatic ring containing one to three N, S and/or O ring atoms with C being the remaining ring atoms. Examples of "aromatic heterocyclic group" include thienyl, furanyl, pyrrolyl, pyrazolyl, imidazolyl, oxazolyl, thiazolyl, isooxazolyl, isothiazolyl, thiadazolyl, pyridinyl, pyridazinyl, pyrimidinyl, pyrazinyl, benzofuranyl, benzo[b]thiophenyl, benzo[c]thiophenyl, indolyl, isoindolyl, isobenzofuranyl, benzimidazolyl, benz[d]isoxazolyl, benzotriazolyl, indazolyl, purinyl, quinolinyl, isoquinolinyl, cinnolinyl, quinazolinyl, quinoxalinyl, phthalazinyl, naphthyridinyl and pteridinyl. "Substituted" aromatic heterocyclic group means an aromatic heterocyclic group substituted by one or more halogen atoms or OH, SH, ($C_1$–$C_6$)alkyl, ($C_2$–$C_6$)alkenyl, ($C_1$–$C_6$)alkoxy, ($C_1$–$C_6$)alkylthio, trifluoromethyl, cyano, nitro, amino, mono-($C_1$–$C_6$)alkyl-amino, di-($C_1$–$C_6$)alkyl-amino, ($C_1$–$C_6$)alkyl-carbonyl, ($C_2$–$C_6$)alkoxy-carbonyl, carboxyl, phenoxy, phenylthio, benzyl, ($C_4$–$C_8$)cycloalkyl, phenyl, phenyl, halogenated phenyl or alkylated phenyl groups.

The term "alkyl" used herein refers to a branched or straight-chain saturated hydrocarbyl group, preferably of 1 to 20 carbon atoms. Examples of "alkyl" include methyl, ethyl, n-propyl, isopropyl, n-butyl, sec-butyl, isobutyl, tert-butyl, n-pentyl, sec-pentyl, tert-pentyl, 2-methylbutyl, 3-methylbutyl, 2,2-dimethylpropyl, n-hexyl, 1-methylpentyl, 2-methylpentyl, 3-methylpentyl, isohexyl, 4,4-dimethylpentyl, n-heptyl, isoheptyl, n-octyl, iso-octyl, n-nonyl, isononyl, n-decyl, n-undecyl, 4-ethyl-3,3-dimethylheptyl, n-dodecyl, n-tridecyl, n-tetradecyl, n-pentadecyl, n-hexadecyl, n-heptadecyl, n-octadecyl, n-nonadecyl and n-icosyl. Preferred examples of "alkyl" are methyl, ethyl, n-propyl, isopropyl, n-butyl, sec-butyl, isobutyl, tert-butyl, n-pentyl, sec-pentyl, tert-pentyl, 2-methylbutyl, 3-methylbutyl, 2,2-dimethylpropyl, n-hexyl, 1-methylpentyl, 2-methylpentyl, 3-methylpentyl, 3,3-dimethylbutyl and isohexyl, n-undecyl, n-tridecyl, n-pentadecyl, n-heptadecyl and n-nonadecyl. More preferably, "alkyl" is a ($C_1$–$C_6$)alkyl, such as methyl, ethyl, n-propyl, isopropyl, n-butyl, sec-butyl, isobutyl, tert-butyl, n-pentyl, sec-pentyl, tert-pentyl, 2-methylbutyl, 3-methylbutyl, 2,2-dimethylpropyl, n-hexyl, 1-methylpentyl, 2-methylpentyl, 3-methylpentyl, 3,3-dimethylbutyl and isohexyl. Even more preferably, "alkyl" is methyl, ethyl, n-propyl, isopropyl, n-butyl, sec-butyl, isobutyl or tert-butyl. "Alkyl" is, much more preferably, methyl or ethyl and, most preferably, methyl. "($C_1$–$C_6$) alkyl" is, preferably, methyl, ethyl, n-propyl, isopropyl, n-butyl, sec-butyl, isobutyl or tert-butyl. More preferably, "($C_1$–$C_6$)alkyl" is methyl or ethyl. Most preferably, "($C_1$–$C_6$)alkyl" is methyl.

A "substituted" alkyl group means an alkyl group having at least one hydrogen atom substituted by a halogen atom or a OH, SH, ($C_1$-$C_6$)alkoxy, ($C_1$-$C_6$)alkylthio, trifluoromethyl, cyano, nitro, amino, mono-$C_1$–$C_6$)alkyl-amino, di-($C_1$–$C_6$)alkyl-amino, ($C_1$–$C_6$)alkyl-carbonyl, ($C_1$–$C_6$)alkoxy-carbonyl, carboxyl, ($C_4$-$C_8$)cycloalkyl, benzoyl, phenoxy, phenylthio, phenyl or phenyl group substituted by one to three halogen, OH, SH, ($C_1$–$C_6$)alkyl, ($C_2$–$C_6$)alkenyl, ($C_4$–$C_8$)cycloalkyl, ($C_1$–$C_6$) alkoxy, ($C_1$–$C_6$)alkylthio, trifluoromethyl, cyano, nitro, amino, mono-($C_1$–$C_6$)alkyl-amino, di-($C_1$–$C_6$)alkyl-amino, ($C_1$–$C_6$)alkyl-carbonyl, ($C_1$-$C_6$)alkoxy-carbonyl or carboxyl groups.

The term "alkylated", in combination with another term, represents the modification of the other term with one or more alkyl groups, with methyl or ethyl preferred, and methyl more preferred. For example, "alkylated phenyl" means a phenyl group substituted with one or more alkyl groups.

In this application, the term "substituted or unsubstituted amino group" includes —$NH_2$, —$NHR_2$, and —$NHR_5$ and —$N(R_6)R_7$, wherein $R_5$, $R_6$ and $R_7$ are each independently an alkyl, alkenyl, alkynyl, cycloalkyl, cycloalkenyl, aromatic hydrocarbon or aromatic heterocyclic group, with the alkyl group preferred, or $R_6$ and $R_7$ together with the attached N atom form a heterocyclic group. When $R_6$ and $R_7$ can optionally together with the attached N atom form a heterocyclic group, the "heterocyclic group" formed by —$N(R_6)R_7$ represents a 5-, 6- or 7-membered ring containing one to three N, O and/or S ring atoms with the balance ring atoms being C, optionally fused with a benzene or 5-, 6- or 7-membered ring containing one to three N, O and/or S ring atoms having C being the balance ring atoms. Examples of such a "heterocyclic group" include piperinyl, piperazinyl, morpholinyl, thiomorpholinyl, indolinyl, isoindolinyl, pyrrolyl, pyrrolidinyl, imidazolyl, oxazolyl, thiazolyl, isooxazolyl, isothiazolyl, thiadazolyl, 1H-pyrazolyl, pyridinyl, pyridazinyl, pyrimidinyl, pyrazinyl, azepinyl, diazepinyl, triazepinyl, indolyl, isoindolyl, indolizinyl, benzimidazolyl, benz[d]isoxazolyl, benzotriazolyl, carbazolyl, indazolyl, purinyl, quinolinyl, isoquinolinyl, quinolizinyl, quinazolinyl, cinnolinyl, quinazolinyl, quinoxalinyl, phthalazinyl, pteridinyl and naphthyridinyl.

The term "halogen" means fluorine, chlorine, bromine or iodine, with chlorine and bromine being preferred, and chlorine being more preferred. The term "halogen", in combination with another term, represents the modification of the other term with one or more fluorine, chlorine, bromine or iodine atoms, with chlorine and bromine being preferred. For example, "halogenated phenyl" means a phenyl group substituted with one or more halogen atoms.

The term "alkenyl" represents a straight-chain or branched unsaturated hydrocarbyl radical, preferably of 2 to 20 carbon atoms. Examples of "alkenyl" are ethenyl, allenyl, 1-propenyl, allyl, butenyl, 1-methylvinyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and icosenyl. Preferred examples of "alkenyl" are ethenyl, 1-propenyl, allyl, 1-methylvinyl and butenyl. Ethenyl, 1-propenyl and allyl are more preferred examples of "alkenyl". Even more preferably, "alkenyl" is ethenyl or 1-propenyl. Most preferably, "alkenyl" is ethenyl.

In this application, "($C_2$–$C_6$)alkenyl" represents a straight-chain or branched unsaturated hydrocarbyl radical of 2 to 6 carbon atoms. Examples of "($C_2$–$C_6$)alkenyl" are ethenyl, allenyl, 1-propenyl, allyl, butenyl, 1-methylvinyl, pentenyl and hexenyl. Preferred examples of "($C_2$–$C_6$) alkenyl" are ethenyl, allenyl, 1-propenyl, allyl and butenyl. More preferably, "($C_2$–$C_6$)alkenyl" is ethenyl, 1-propenyl or allyl. Even more preferably, "($C_2$–$C_6$)alkenyl" is ethenyl or 1-propenyl. Most preferably, "($C_2$–$C_6$)alkenyl" is ethenyl. In some of the embodiments of the compound according to Formula (1), preferably, $Ar_1$ is an unsubstituted aromatic hydrocarbon group (e.g. phenylene, naphthalenediyl and anthracenediyl) or two identical unsaturated aromatic hydrocarbon groups directly linked together (e.g. biphenyldiyl); R1, R2 and R3 each independently represents a H atom or substituted amino group (e.g. piperidinyl, piperazinyl and morpholinyl, with piperidinyl preferred), or two of R1, R2 and R3 both represent a H atom and the remaining one represents a F atom or CN, unsubstituted alkyl, unsubstituted aromatic hydrocarbon, or substituted or unsubstituted amino group; and R4 represents an unsubstituted alkyl (e.g. ($C_1$–$C_6$)alkyl such as methyl or ethyl, with methyl preferred) or unsubstituted aromatic hydrocarbon group (e.g phenyl). In these embodiments, more preferably, $Ar_1$ is an unsubstituted aromatic hydrocarbon group or two identical unsaturated aromatic hydrocarbon groups directly linked together; R1, R2 and R3 each independently represents a H atom or substituted amino group, or two of R1, R2 and R3 both represent a H atom and the remaining one represents a substituted amino group.

The compound of Formula (1) can be considered as containing two indole-based units, one of which is represented by Formula (2), connected by an arylamine unit represented by Formula (3),

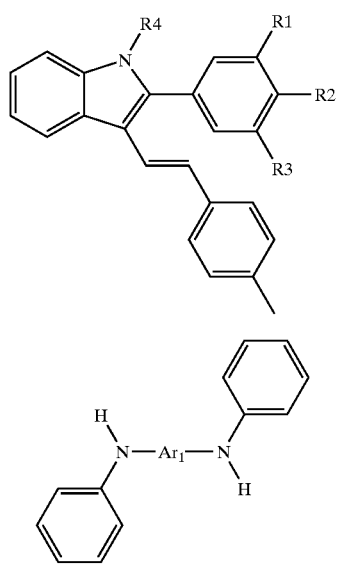

wherein R1 to R4 and Ar1 have the same meanings as above. Each indole-based unit of Formula (2) acts a as light emitting unit, wherein the color of the light emitted can be adjusted by changing the connecting unit represented by Formula (3).

Example of Ar1 are shown below.

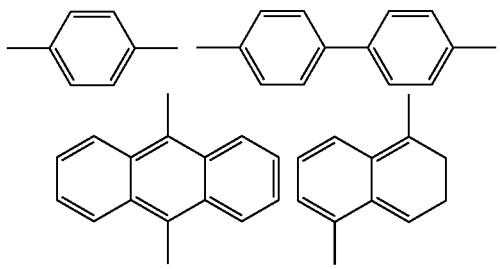

Referring to the following reaction schemes, synthesis methods which can be used to obtain the indole-based compounds represented by Formula (1) of the present invention will be described below.

The indole-based unit, which is the main skeleton of the indole-based compound of Formula (1), can be formed by the process of Scheme (1):

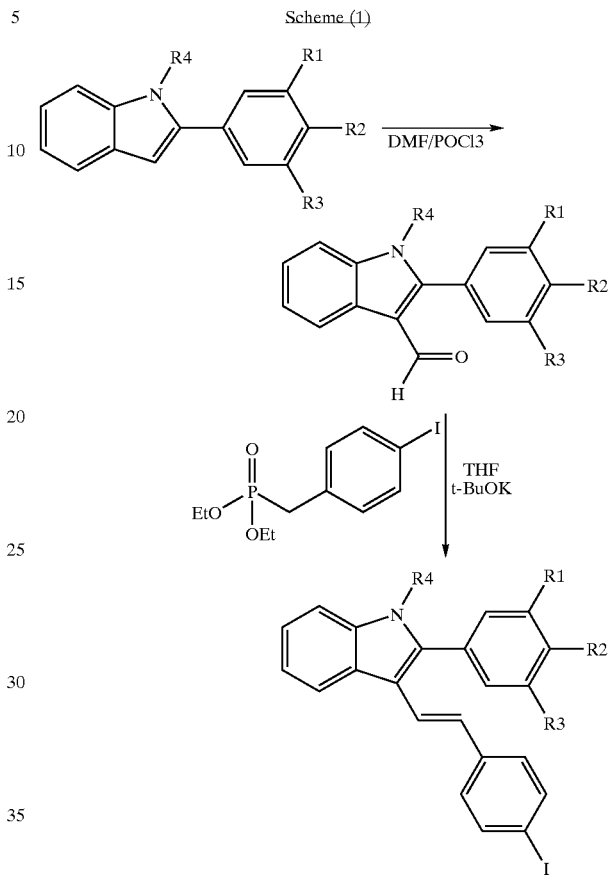

wherein R1, R2, R3 and R4 are as defined above.

The indole-based unit is reacted with an arylamine of Formula (3) to yield the indole-based compound represented by Formula (1) as shown in the process according to Scheme (2).

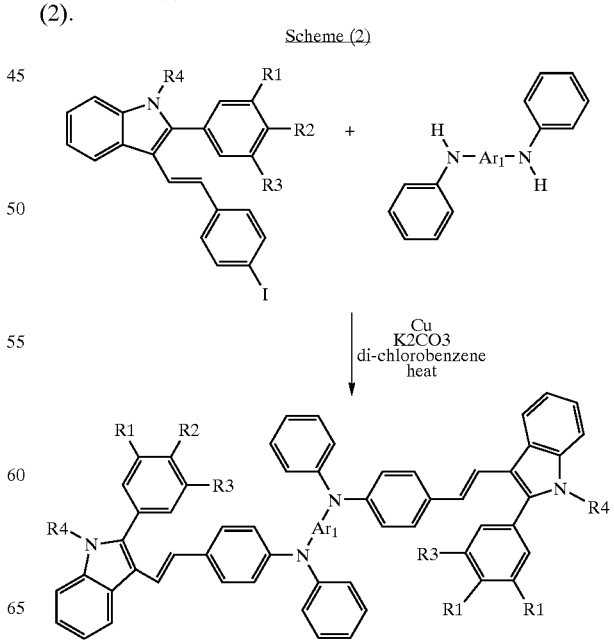

Examples of indole-based compounds represented by Formula (1) are shown below.
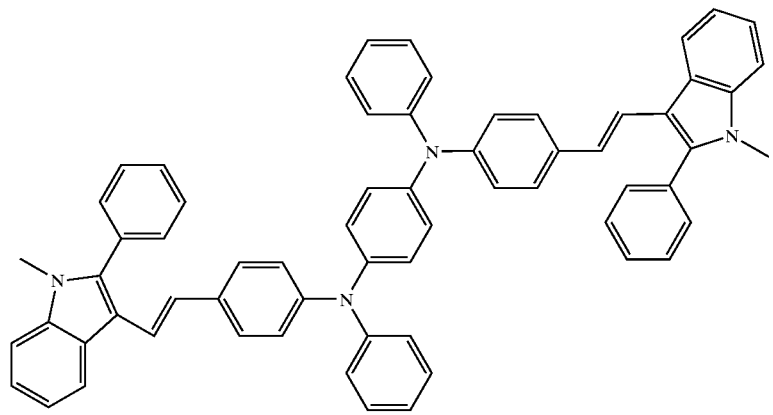
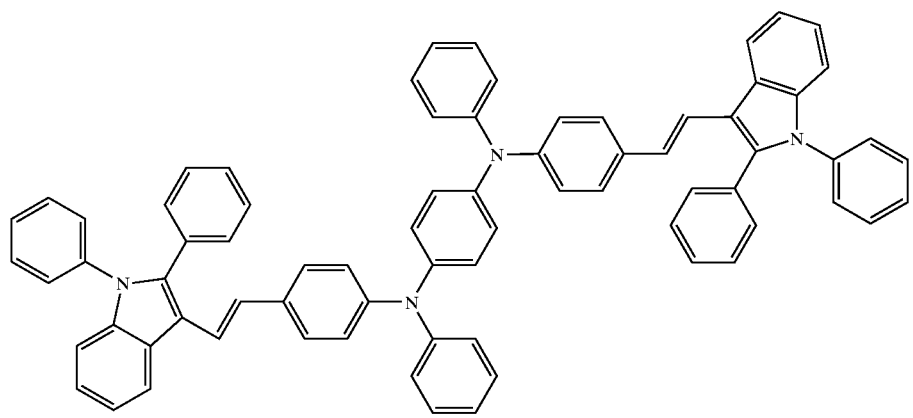
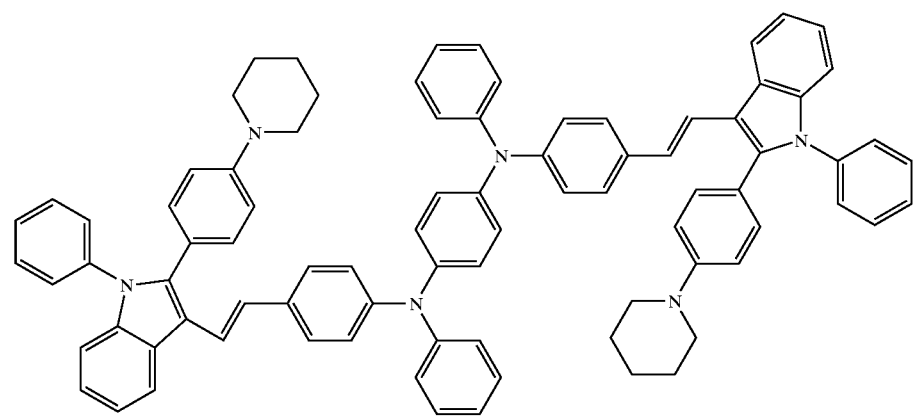

-continued
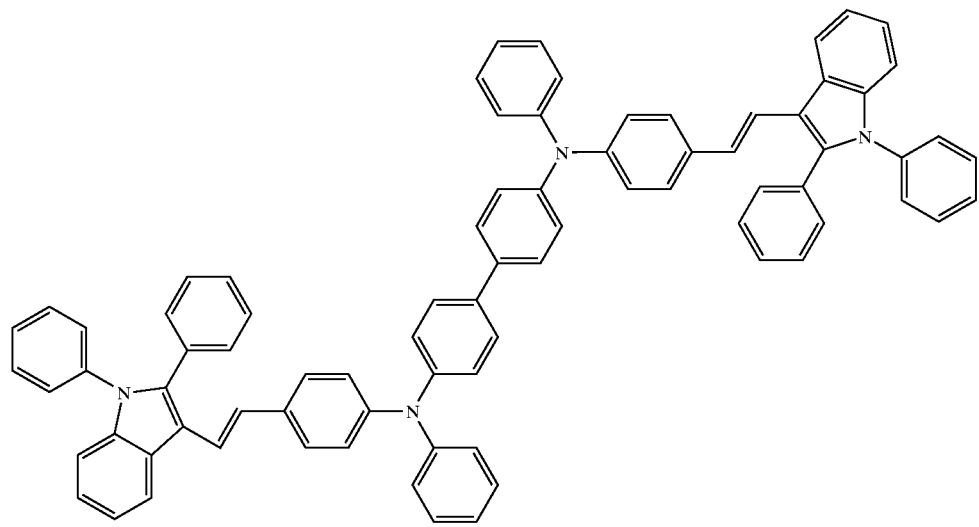
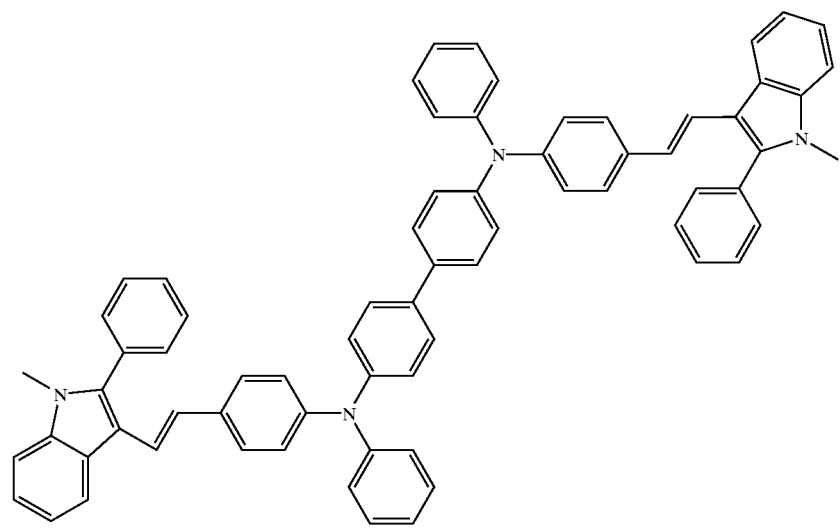
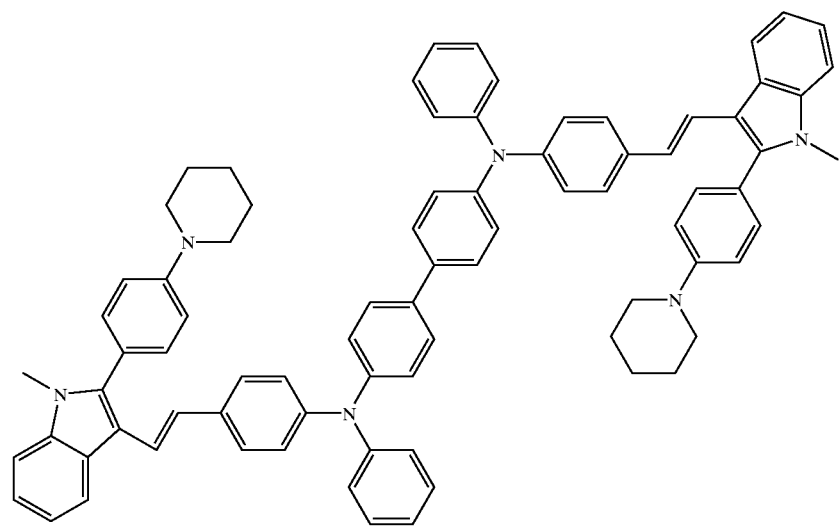

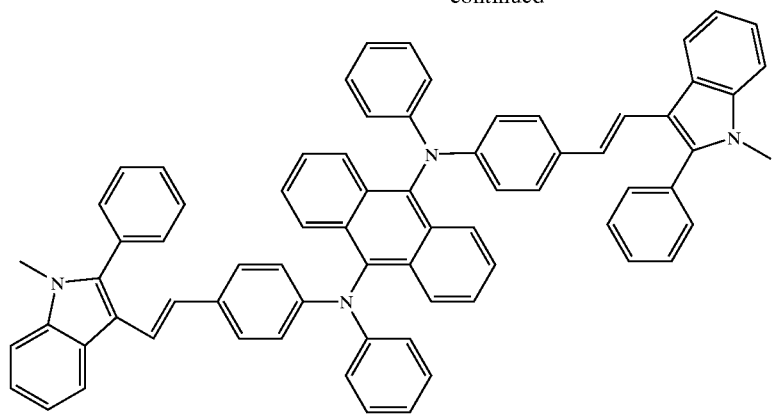

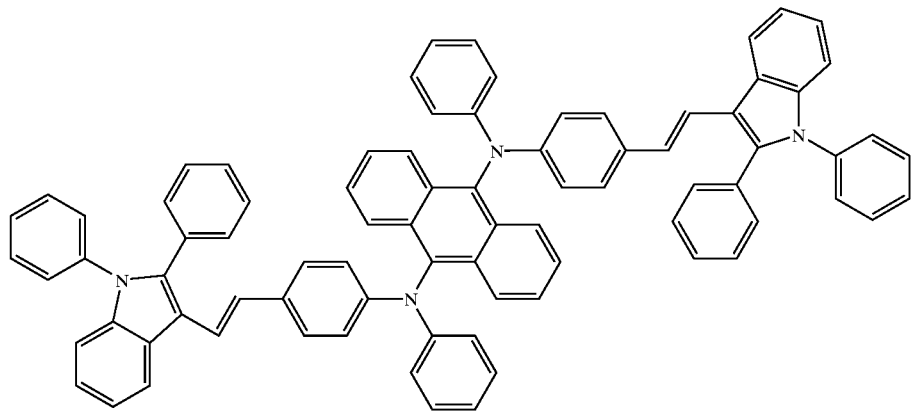

The organic EL device according to the present invention has a multi-layered structure including a light emitting layer, one or more hole transporting layers, and one or more electron transporting layers.

The hole transporting layer contains one or more organic layers including a hole injection layer, which increases the light emitting performance by improving the hole injection from the anode into the organic layers, and improving the contact of anode with the organic layers. Typical compounds for the hole injection layer include porphyrin compounds (U.S. Pat. Nos. 3,935,031 or 4,356,429) having the following illustrative structure:

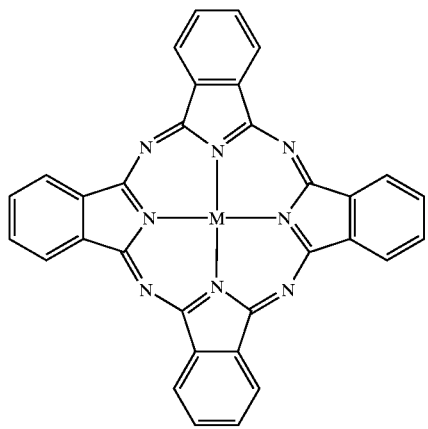

wherein M is a metal, metal oxide, or metal halide.

Aromatic tertiary amine compounds (U.S. Pat. Nos. 4,127,412 and 6,074,734) suitable for forming both hole injection materials and hole transporting materials include diarylamine or triarylamine having the following structures:

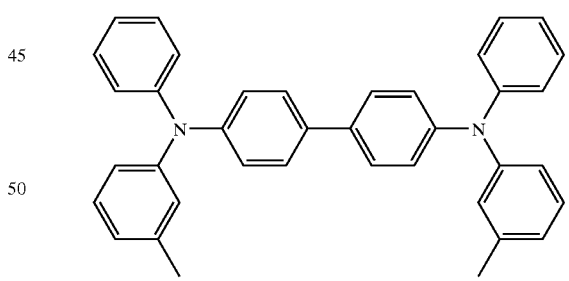

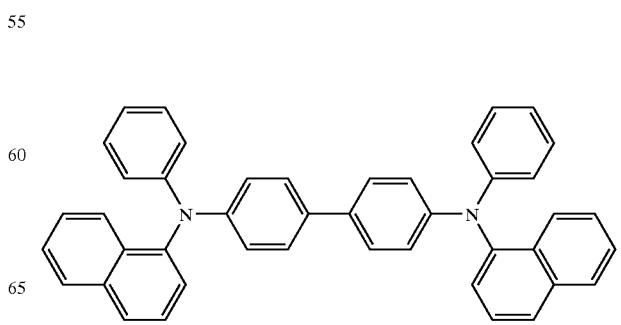

-continued

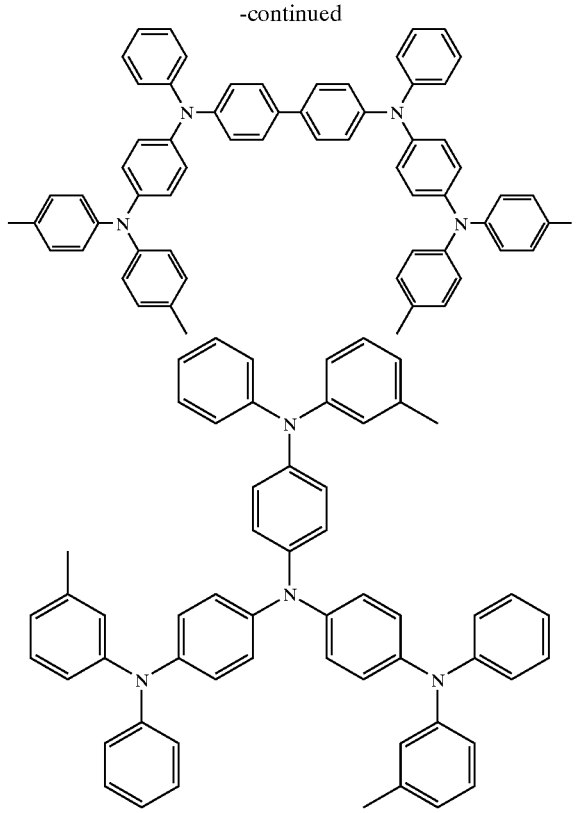

The electron transporting layer contains one or more organic layers to inject and transport electrons from the cathode into the organic layers. An electron injection layer increases the light emitting property by improving the electron injection performance from the cathode into the organic layers. Typical compounds for the electron injection materials include oxadiazole compounds, triazine compounds and triazole compounds. Examples of these compounds are shown below:

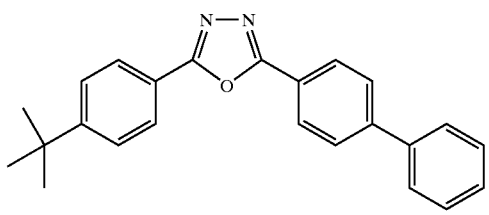

-continued

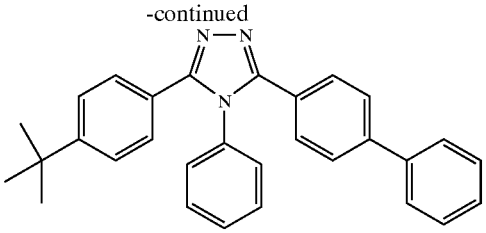

The cathode for the organic EL device can be formed by vacuum deposition of a single metal or a combination of two metals. Typical examples of a single metal for making the cathode include aluminum (Al), magnesium (Mg), calcium (Ca) and lithium (Li). Common examples of the combination of two metals used for making the cathode include aluminum-lithium (Al—Li) and magnesium-silver (Mg—Ag). In the present invention, Al is preferred as the single metal for forming the cathode.

The anode for the organic EL device can be formed by coating a conducting material on a substrate. Glass is a common and widely used substrate. In this invention, indium-tin-oxide (ITO) is preferably used as the conducting material on a glass substrate for forming the anode.

In the present invention, the organic EL device can be manufactured by vacuum deposition of organic materials to form one or more organic layers on an anode or cathode layer, followed by the formation of a cathode or anode layer (depending on whether the organic materials are first deposited on the anode or cathode layer) to obtain the organic EL device having a structure of ITO (anode)/organic layers/Al (cathode). The organic layers can include a hole injection layer, hole transporting layer, emitting layer and electron injection layer. The total thickness of organic layers in this present invention ranges from about 5 nm to about 500 nm. The thickness of the cathode is preferably about 150 nm to about 250 nm. When a DC power of 5 to 25 voltage is applied to the organic EL device of the present invention, blue light emission is obtained.

The present invention will hereafter be illustrated in detail by working examples, but the present invention is not limited by the following working examples. The scope of the invention should be measured by the claims, not the working examples.

Synthesis Example 1

An embodiment, Compound (A), of the indole-based compounds of Formula (1) having the following structure:

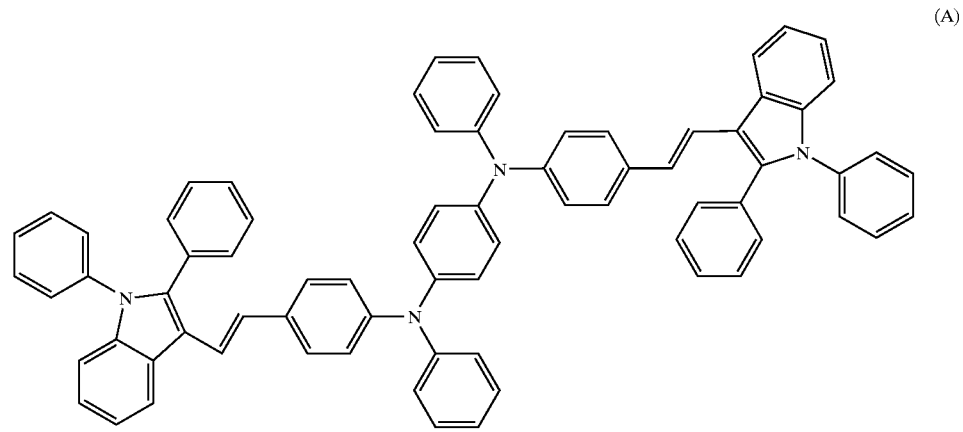

(A)

was synthesized below. An indole-based unit, Compound (a), of Compound (A) was first prepared according to the process of Scheme (3):

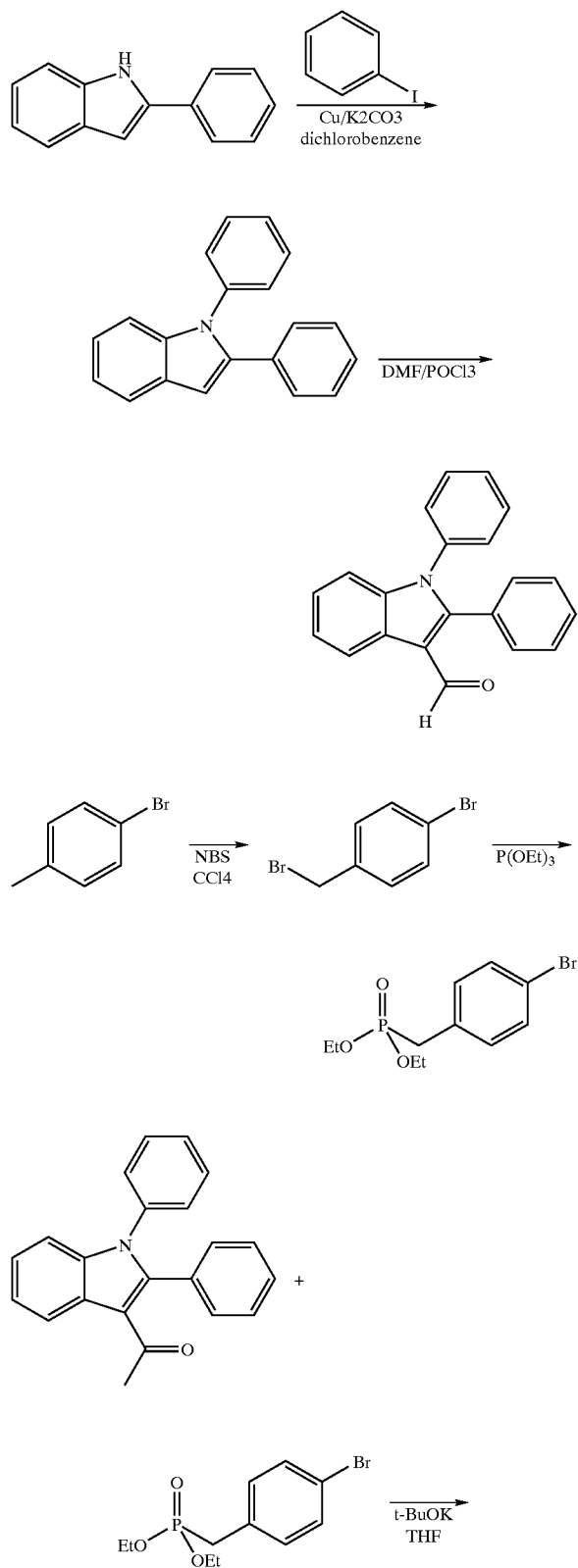

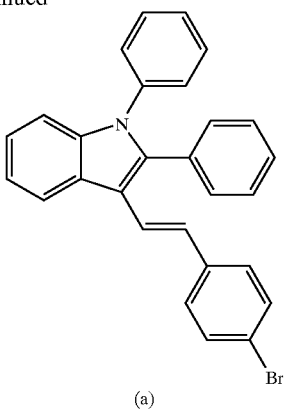

(a)

Figure 2:
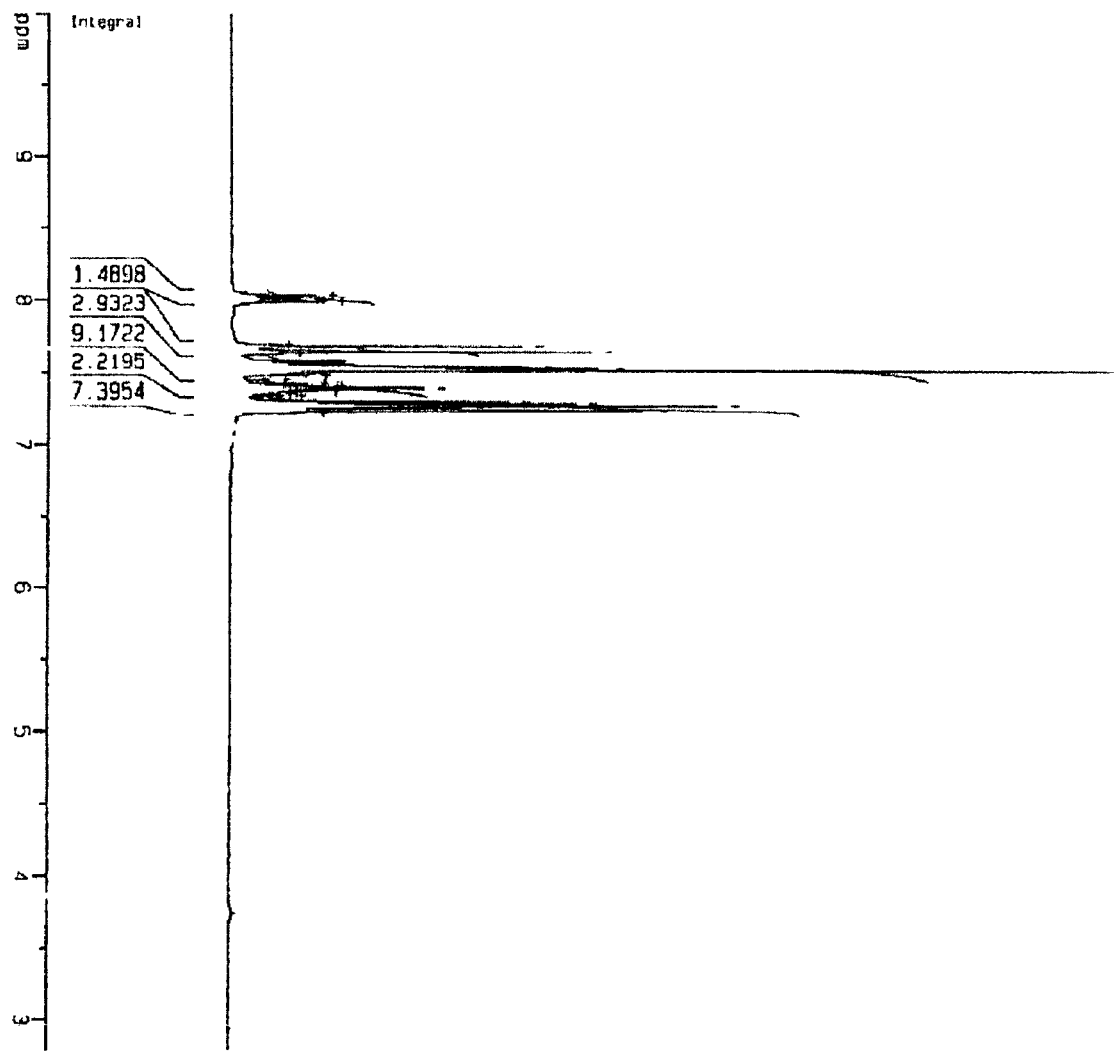
FIG. 2 illustrates the $^1$H-NMR of Compound (a) disclosed below.

The indole-based unit, Compound (a), was obtained as a light yellow powder, $^1$H-NMR (CDCl$_3$, TMS) δ(ppm)=7.25–7.58 (m, 17H,), 7.65–7.68 (d, 2H,), 8.02 (d, 1H), with a NMR spectrum as shown in FIG. 2. The indole-based unit, Compound (a), was then reacted with an arylamine unit of Formula (3), wherein Ar$_1$ was phenylene, according to the process of Scheme (4) to prepare Compound (A):

Scheme (4)

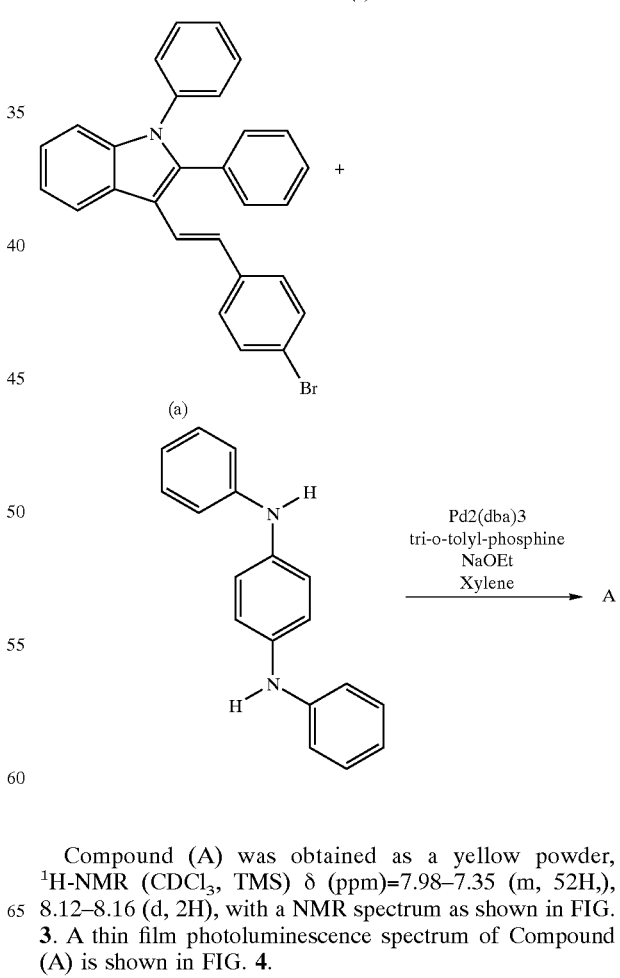

Figure 3:
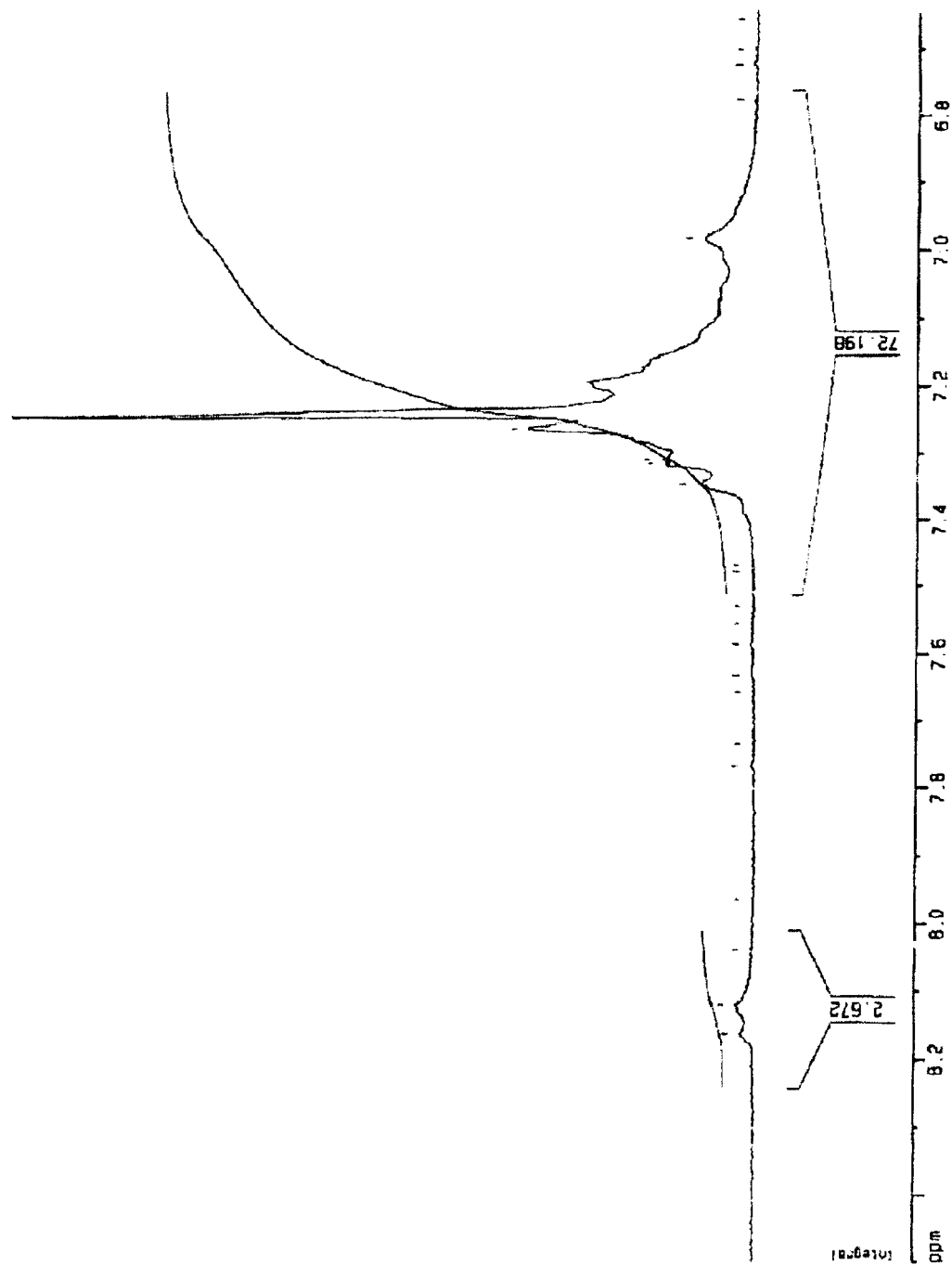
FIG. 3 illustrates the $^1$H-NMR of Compound (A) disclosed below.

Compound (A) was obtained as a yellow powder, $^1$H-NMR (CDCl$_3$, TMS) δ (ppm)=7.98–7.35 (m, 52H,), 8.12–8.16 (d, 2H), with a NMR spectrum as shown in FIG. 3. A thin film photoluminescence spectrum of Compound (A) is shown in FIG. 4.

Device Example 1

An organic EL device was made using Compound (A) as the light emitting material. The organic EL device of this example had glass substrates with an ITO electrode 11 having a surface resistance of 20Ω as the anode.

Similar to the structure shown in FIG. 1, a 60 nm organic layer 12 was formed on the ITO electrode 11 as a hole-transporting layer by vacuum deposition of NPB having the following structure:

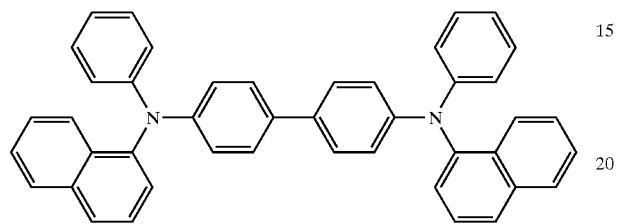

Over the hole-transporting layer 12, a 40 nm emitting layer 13 was formed by vacuum co-deposition of Compound (H), the formula for which is shown below, as a host material and Compound (A) as a dopant material with a dopant concentration of 3% on the hole-transporting layer 12.

(H)

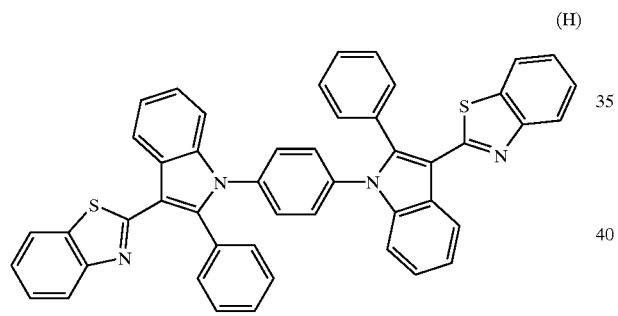

Then, a 20 nm electron-transporting layer 14 was formed on the emitting layer 13 by vacuum deposition of Bphen having the following structure:

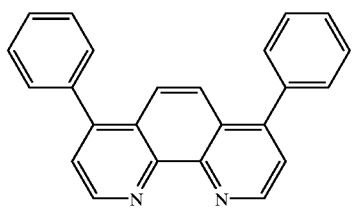

Figure 6:
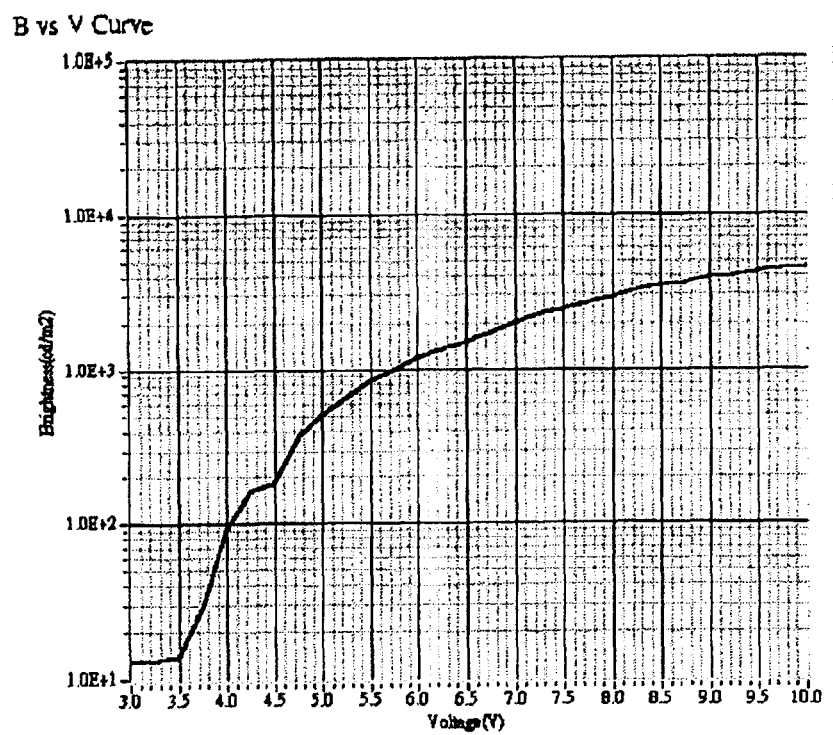
FIG. 6 illustrates the BV curve of Device Example 1.
Figure 7:
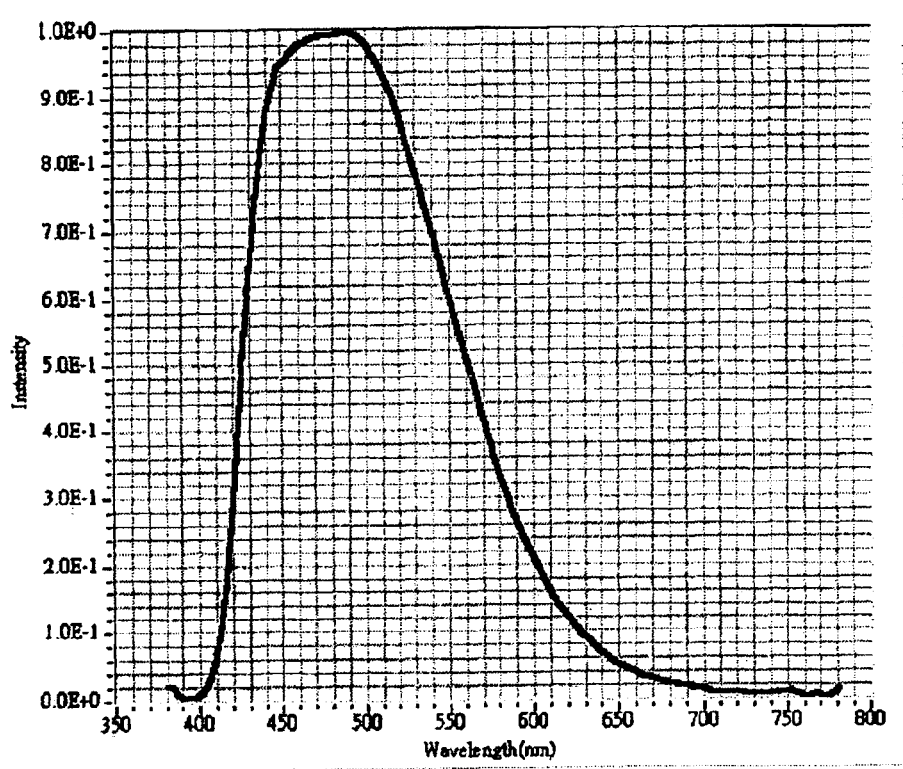
FIG. 7 illustrates the EL spectrum of Device Example 1.
Figure 8:
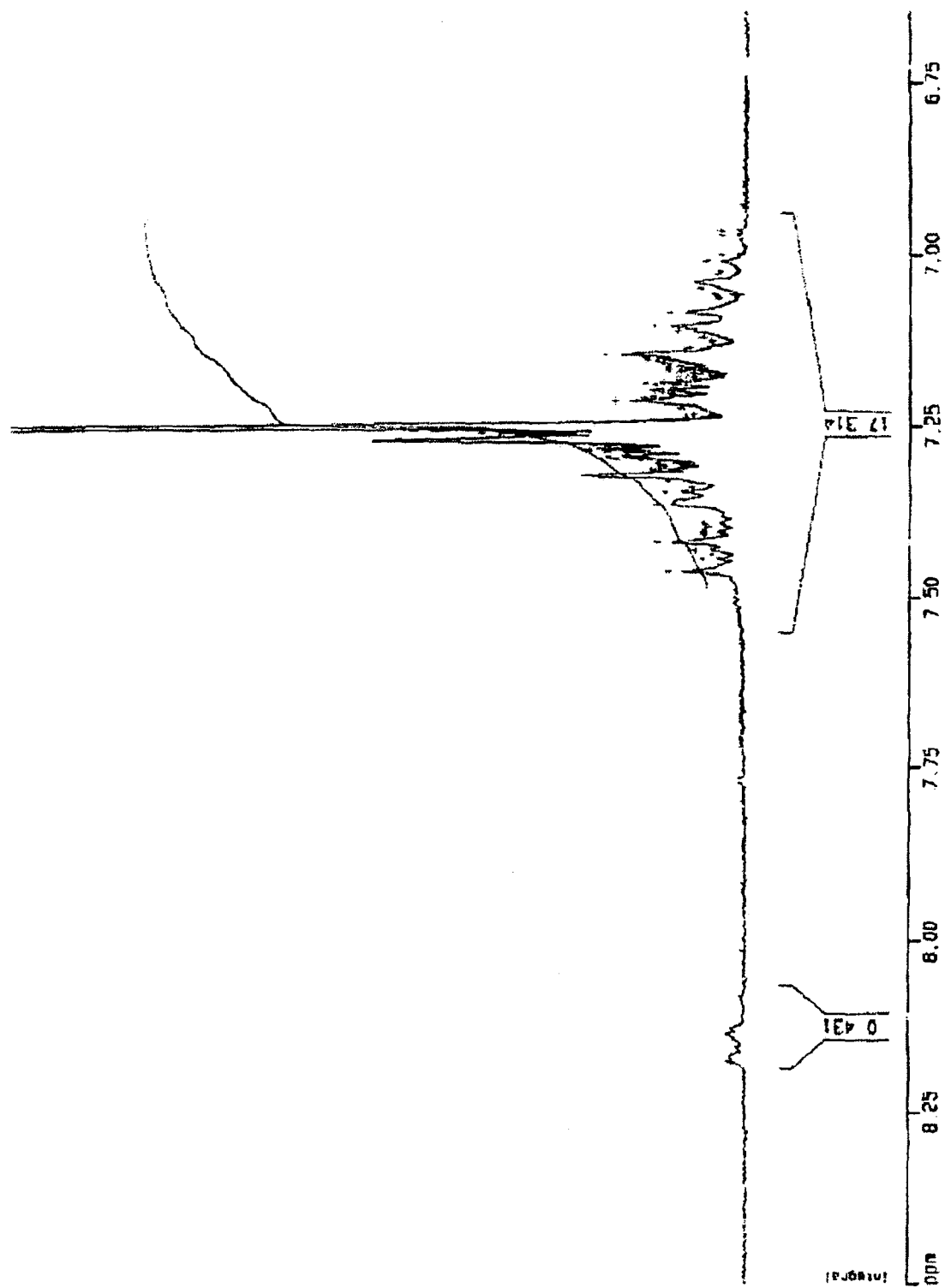
FIG. 8 illustrates the $^1$H-NMR of Compound (B) disclosed below.

On the electron-transporting layer 14, a 0.8 nm electron-injection layer 15 was formed by vacuum deposition of LiF. Finally, a 200 nm aluminum cathode 16 was formed by vacuum deposition on the electron-injection layer 15. When a DC voltage was applied to the resulting device, a light-blue light emission was obtained. A current-voltage curve, Brightness-Voltage curve and EL spectrum were obtained with the organic EL device as shown in FIG. 5 to FIG. 7.

The EL spectrum of Compound (H) had a maximum peak at 435 nm based on previous determinations. It was different from the EL spectrum of Compound (A) which was almost identical with the PI, spectrum of Compound (A). Hence, it was confirmed that the light-blue color light was emitted from a novel indole-based compound.

Synthesis Example 2

Another embodiment, Compound (B), of the indole-based compounds of Formula (1) having the structure:

(B)

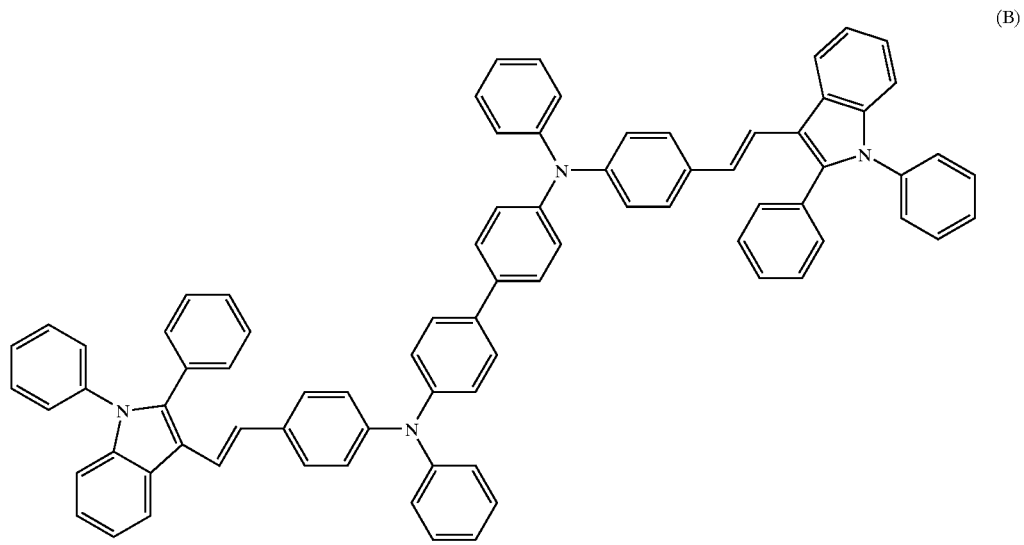

was prepared according to the process of Scheme (5):

Scheme (5)

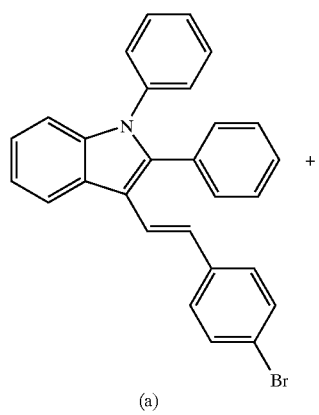

(a)

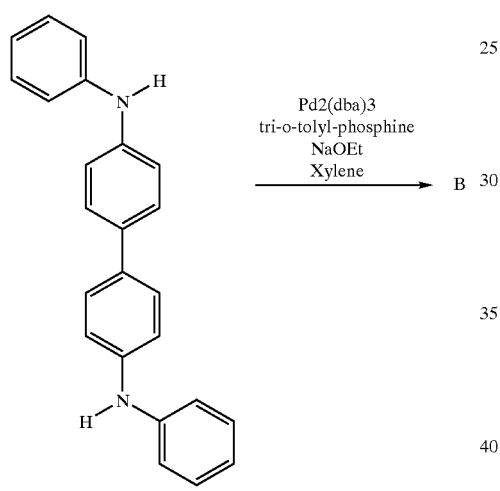

Compound (B) was obtained as a yellow powder, $^1$H-NMR (CDCl$_3$, TMS) δ (ppm) 7.1–7.4 (m, 56H, aromatic H), 8.2 (d, 2H, aromatic H). The NMR spectrum is shown in FIG. (8) and a thin The PL spectrum is shown in FIG. (9).

Device Example 2

Figure 11:
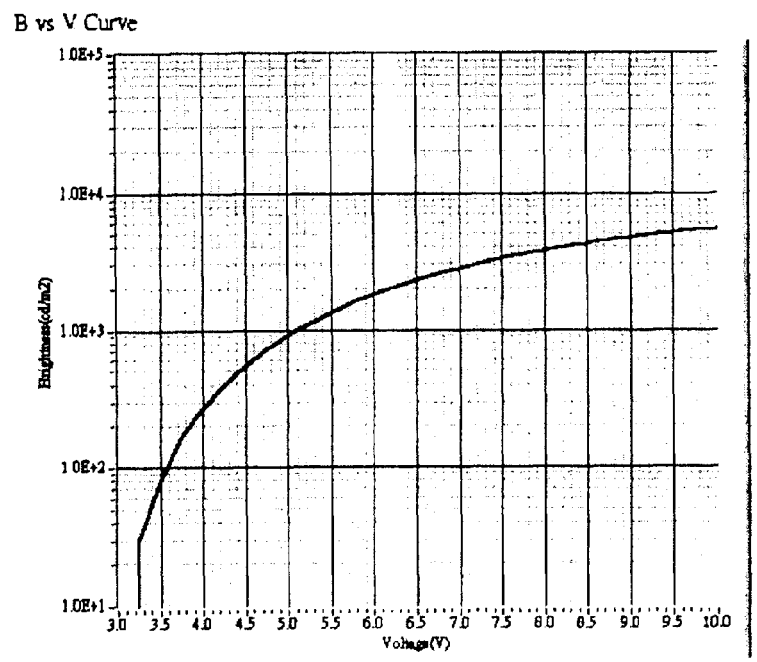
FIG. 11 illustrates the BV curve of Device Example 2.
Figure 12:
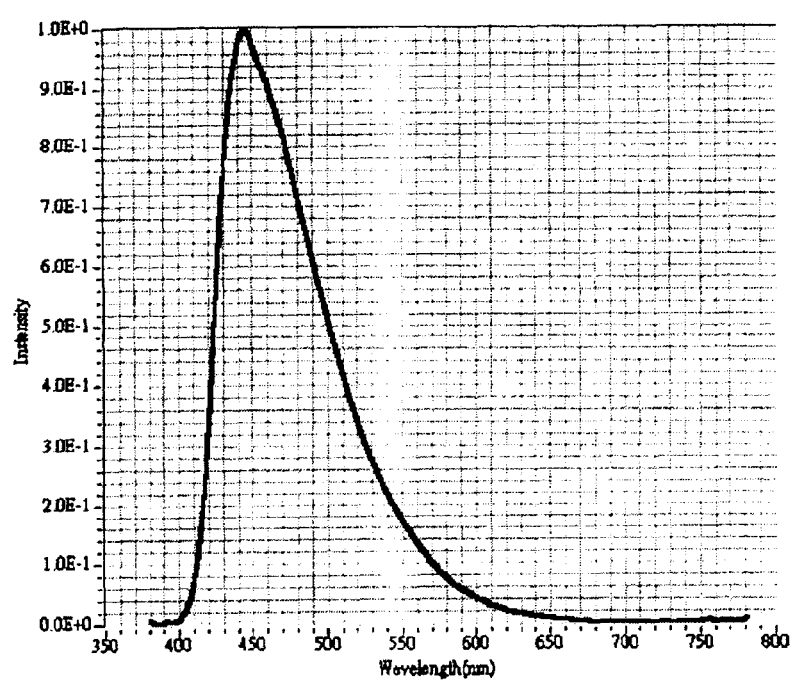
FIG. 12 illustrates the EL spectrum of Device Example 2.

An organic EL device using Compound (B) as a light emitting material was prepared in this example. In a manner similar to the making of Device Example 1, an emitting layer was formed by vacuum co-deposition of Compound (H) and Compound (B) at a dopant concentration of 3%. A current-voltage curve, Brightness-voltage curve and EL spectrum were obtained with the organic EL device as shown in FIG. 10 to FIG. 12 The EL spectrum of Compound (H) had a maximum peak at 435 nm based on previous determinations. It was different from the EL spectrum of Compound (B) which was almost identical with the PL spectrum. Hence, it was confirmed that the blue color light was emitted from a novel indole-based compound.

Upon a review of Device Examples 1 and 2 having EL spectrum peaks at around 500 nm and 460 nm, it was noted that the novel indole-based compound of Formula (1) shown below can be a light emitting material:

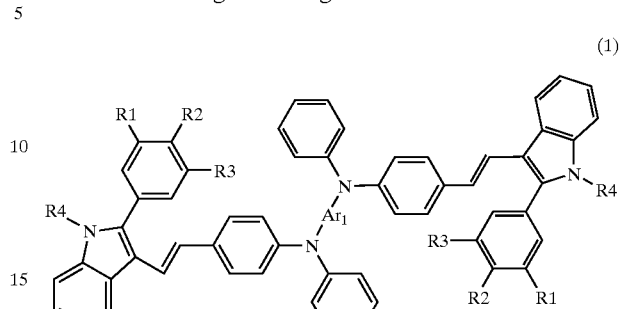

(1)

wherein the indole-based unit of Formula (2) shown below can be the light emitting unit.

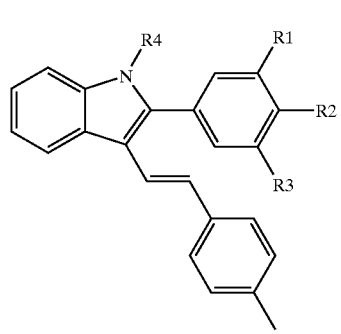

(2)

In Formula (1), the connecting unit of Formula (3) with the following structure can two functions: to connect two indole-based units of Formula (2) and to adjust the light emitting color of these emitting materials:

(3)

What is claimed is:

1. An organic EL device having a multi-layered structure comprising:

an anode;

a cathode; and at least one organic layer between said anode and cathode, wherein said at least one organic layer comprises a compound represented by Formula (1):

(1)

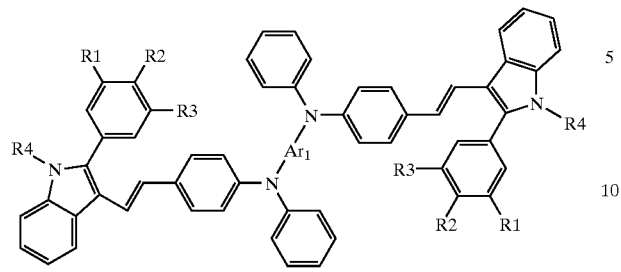

wherein Ar₁ represents a substituted or unsubstituted aromatic hydrocarbon group, a group formed by two aromatic hydrocarbon groups directly linked together, wherein the two aromatic hydrocarbon groups are independently substituted or unsubstituted, a substituted or unsubstituted aromatic heterocyclic group, a group formed by two aromatic heterocyclic groups directly linked together, wherein the two aromatic heterocyclic groups are independently substituted or unsubstituted, or a group formed by an optionally substituted aromatic hydrocarbon group directly linked with an optionally substituted aromatic heterocyclic group; R1, R2 and R3 each independently represents a H atom, F atom, CN group, substituted or unsubstituted alkyl group, substituted or unsubstituted aromatic hydrocarbon group, or substituted or unsubstituted amino group; any two of R1, R2 and R3 may form an aromatic heterocyclic or hydrocarbon ring; R4 represents a substituted or unsubstituted alkyl group, substituted or unsubstituted aromatic hydrocarbon group, or substituted or unsubstituted aromatic heterocyclic group.

2. The organic EL device of claim 1, wherein the compound represented by Formula (1) is a compound of Formula (1A):

(1A)

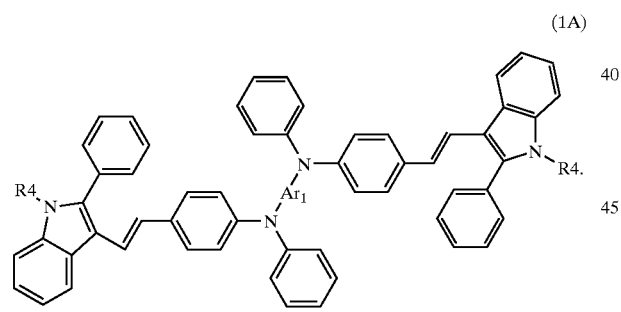

3. An organic EL device according to claim 2, wherein Ar₁ is a group represented by Formula (I), (J), (K) or (L):

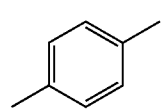  I

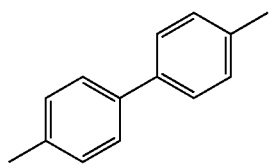  J

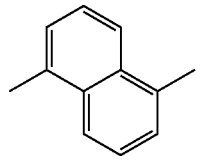  K

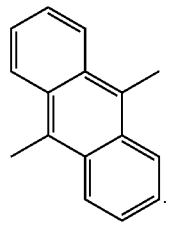  L

4. The organic EL device of claim 2, wherein said at least one organic layer comprising the compound represented by Formula (1) is a light emitting layer.

5. The organic EL device of claim 1, wherein the compound represented by Formula (1) is a compound of Formula (1B):

(1B)

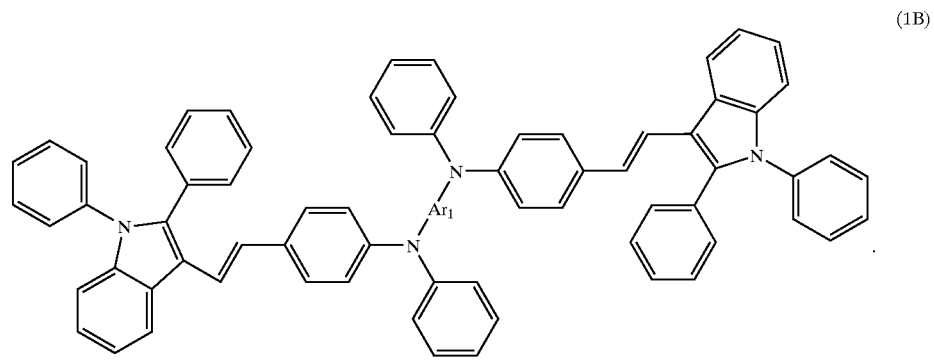

6. An organic EL device according to claim 5, wherein $Ar_1$ is a group represented by Formula (I), (J), (K) or (L):

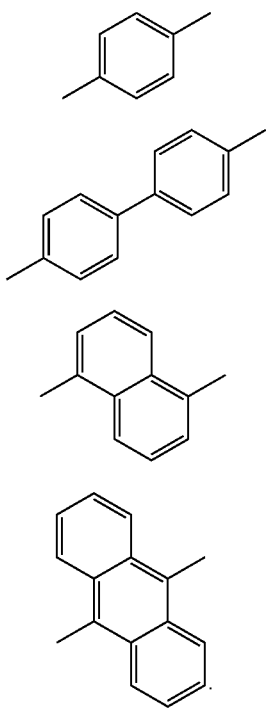

7. The organic EL device of claim 5, wherein said at least one organic layer comprising the compound represented by Fomula (1) is a light emitting layer.

8. An organic EL device according to claim 1, wherein $Ar_1$ is a group represented by Formula (I), (J), (K), or (L):

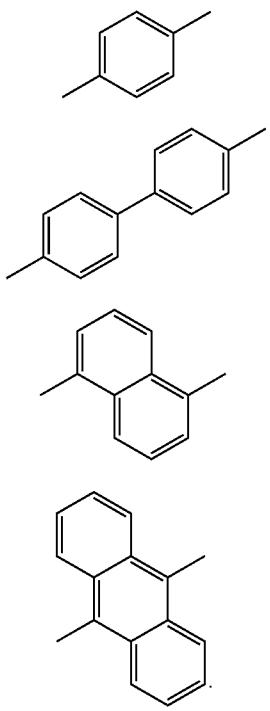

9. The organic EL device of claim 1, wherein said at least one organic layer comprising the compound represented by Formula (1) is a light emitting layer.

10. The EL device of claim 1, wherein $Ar_1$ is an unsubstituted aromatic hydrocarbon group, a group formed by two identical unsubstituted aromatic hydrocarbon groups directly linked together, an unsubstituted aromatic heterocyclic group, or a group formed by two identical unsubstituted aromatic heterocyclic groups directly linked together.

11. The organic EL device of claim 10, wherein $Ar_1$ is an unsubstituted aromatic hydrocarbon group or a group formed by two identical unsaturated aromatic hydrocarbon group directly linked together.

12. The organic EL device of claim 11, wherein $Ar_1$ is an unsubstituted aromatic hydrocarbon group.

13. The organic EL device of claim 12, wherein $Ar_1$ is phenylene, naphthalenediyl or anthracenediyl.

14. The organic EL device of claim 13, wherein $Ar_1$ is 1,4-phenylene.

15. The organic EL device of claim 11, wherein $Ar_1$ is a group formed by two identical unsatured aromatic hydrocarbon groups directly linked together.

16. The organic EL device of claim 15, wherein $Ar_1$ is 4,4'-biphenyldiyl.

17. The organic EL device of claim 1, wherein R1, R2 and R3 each independently represents a H atom, unsubstituted alkyl group, unsubstituted aromatic hydrocarbon group, $-NH_2$, $-NHR_5$ or $-N(R_6)R_7$, wherein $R_5$, $R_6$ and $R_7$ are each independently an alkyl, alkenyl, alkynyl, cycloalkyl, cycloalkenyl, aromatic hydrocarbon or aromatic heterocyclic group, or $R_6$ and $R_7$ together with the attached N atom form a heterocyclic group.

18. The organic EL device of claim 17, wherein R1, R2 and R3 each independently represents a H atom or $-N(R_6)R_7$, wherein $R_6$ and $R_7$ together with the attached N atom form a heterocyclic group.

19. The organic EL device of claim 18, wherein R1, R2 and R3 each represents a H atom or piperidinyl group.

20. The organic EL device of claim 1, wherein $Ar_1$ is an unsubstituted aromatic hydrocarbon group or two identical unsaturated aromatic hydrocarbon groups directly linked together; R1, R2 and R3 each represents a H atom, or two of R1, R2 and R3 represent H atoms and the remaining one represents a F atom or CN, unsubstituted alkyl, unsubstituted aromatic hydrocarbon, or substituted or unsubstituted amino group; and R4 represents an unsubstituted alkyl or unsubstituted aromatic hydrocarbon group.

21. The organic EL device of claim 20, wherein $Ar_1$ is an unsubstituted aromatic hydrocarbon group or two identical unsaturated aromatic hydrocarbon groups directly linked together; R1, R2 and R3 each represents a H atom, or two of R1, R2 and R3 represent H atoms and the remaining one represents a substituted amino group; and R4 represents an unsubstituted aromatic hydrocarbon group.

22. The organic EL device of claim 21, wherein R4 is methyl or phenyl.

23. The organic EL device of claim 22, wherein R4 is phenyl.

24. The organic EL device of claim 22, wherein the compound represented by Formula (1) is a compound of Formula (4), (5), (6), (7), (8), (9), (10) or (11):

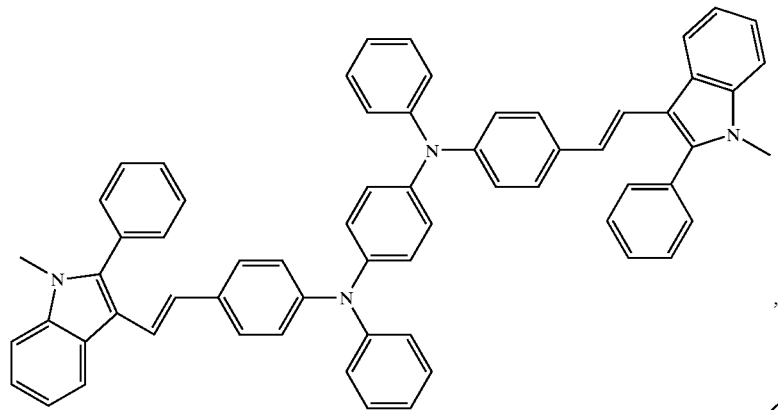
(4)
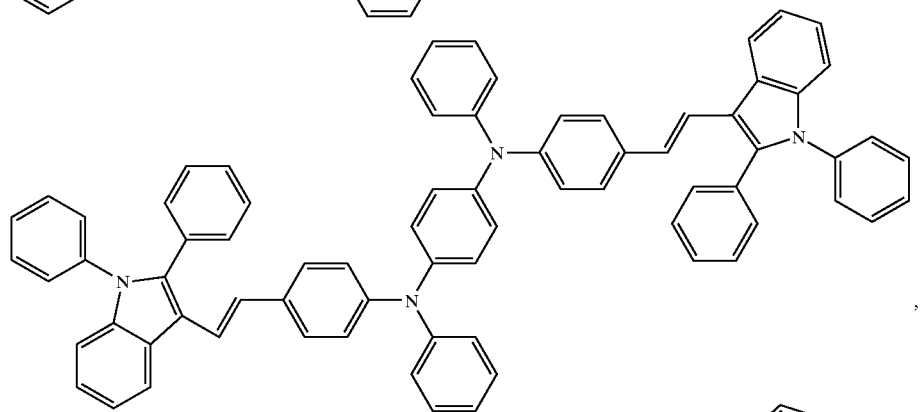
(5)
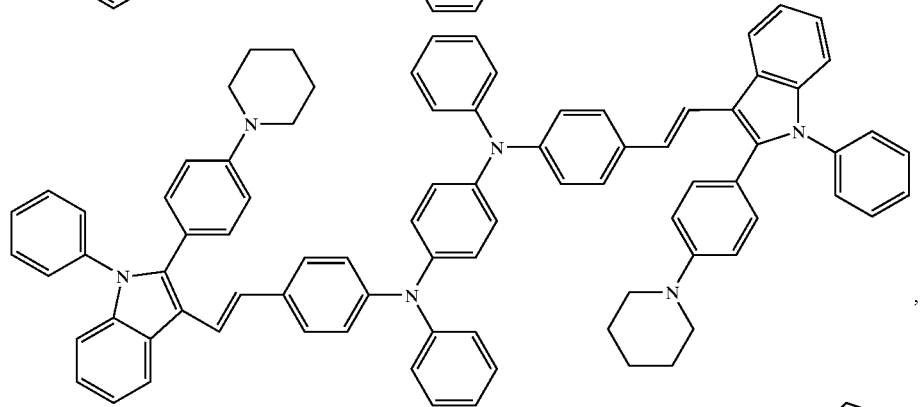
(6)
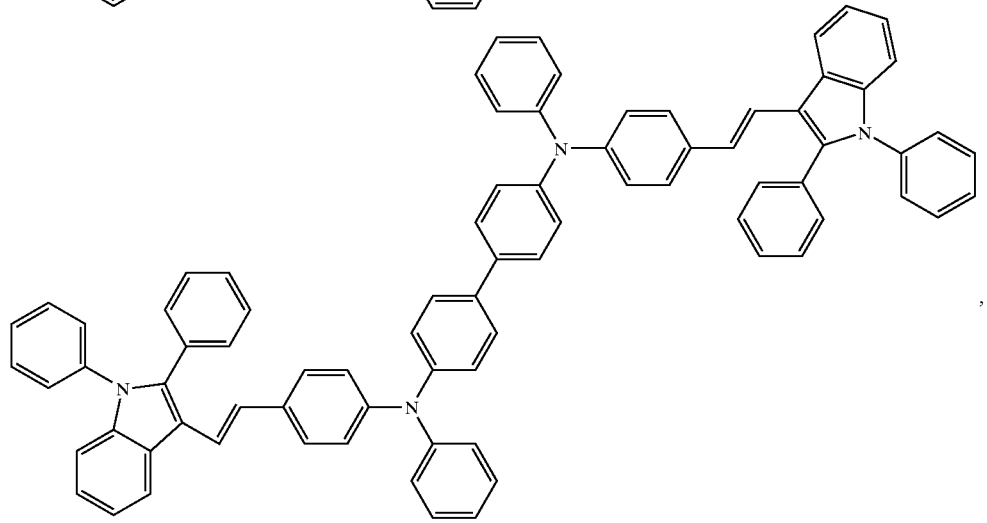
(7)

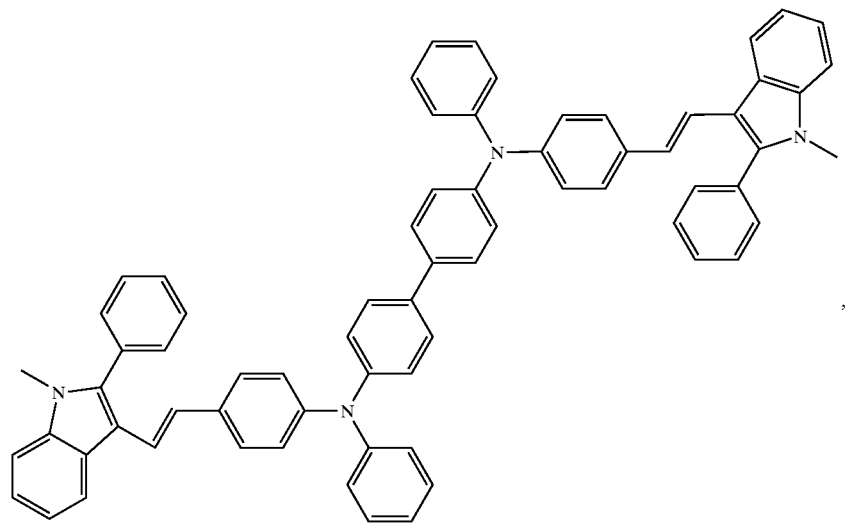
(8)
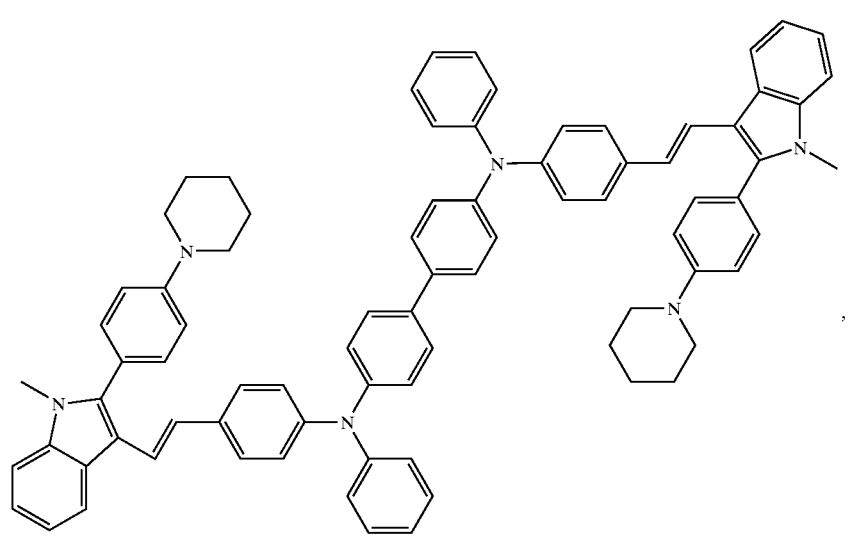
(9)
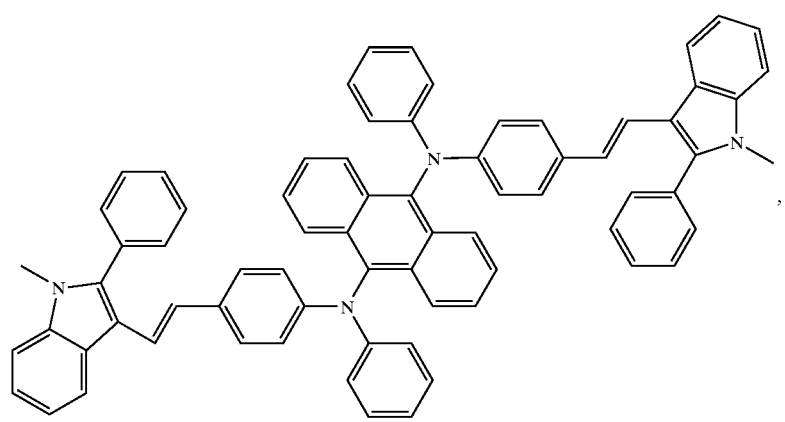
(10)

(11)

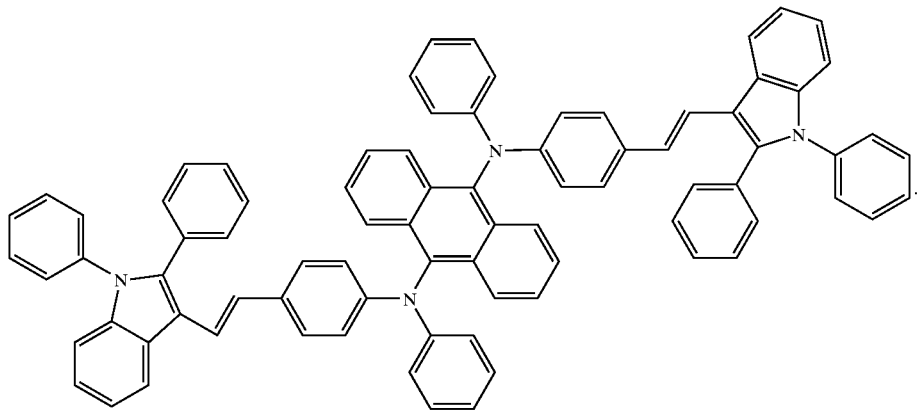

25. The organic EL device of claim 24, wherein the compound represented by Formula (1) is the compound of Formula (5) or (7).

26. The organic EL device of claim 1, wherein said at least one organic layer comprising the compound represented by Formula (1) is at least one light emitting layer, said organic EL device further comprising at least one hole transporting layer, at least one electron transporting layer, and/or at least one electron-injection layer between said anode and cathode.

27. A compound represented by Formula (1):

(1)

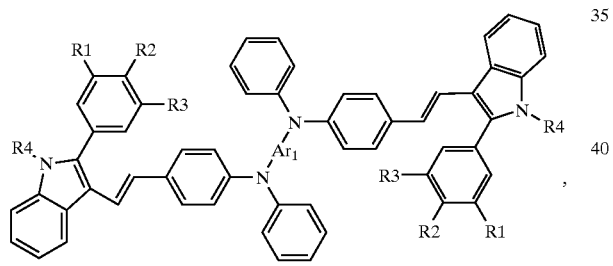

wherein Ar₁ represents a substituted or unsubstituted aromatic hydrocarbon group, a group formed by two aromatic hydrocarbon groups directly linked together, wherein the two aromatic hydrocarbon groups are independently substituted or unsubstituted,or a substituted or unsubstituted aromatic heterocyclic group, a group formed by two aromatic heterocyclic groups directly linked together, wherein the two aromatic heterocyclic groups are independently substituted or unsubstituted, or a group formed by an optionally substituted aromatic hydrocarbon group directly linked with an optionally substituted aromatic heterocyclic group; R1, R2 and R3 each independently represents a H atom, a F atom, a CN group, a substituted or unsubstituted alkyl group, a substituted or unsubstituted aromatic hydrocarbon group, or a substituted or unsubstituted amino group; any two of R1, R2 and R3 may form an aromatic heterocyclic or hydrocarbon ring; R4 represents a substituted or unsubstituted alkyl group, a substituted or unsubstituted aromatic hydrocarbon group, or a substituted or unsubstituted aromatic heterocyclic group.

28. The compound of claim 27, represented by Formula (1A):

(1A)

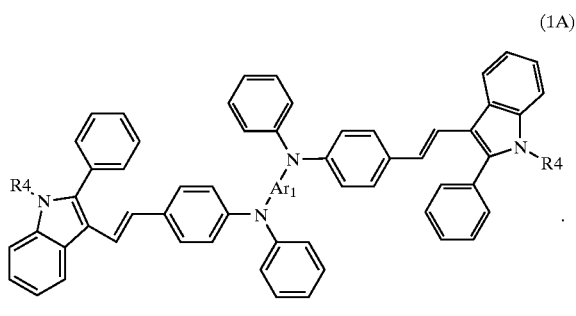

29. The compound according to claim 28, wherein Ar₁ is a group represented by Formula (I), (J), (K) or (L):

I

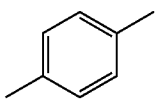

J

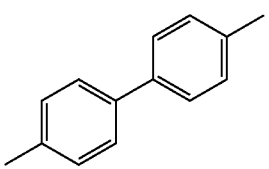

K

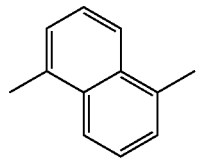

L

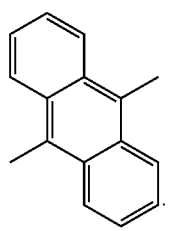

30. The compound of claim 27, represented by Formula (1B):

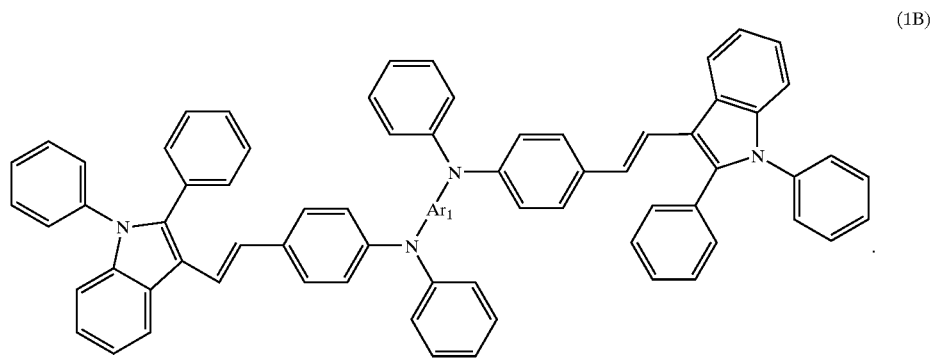

(1B)

31. A compound according to claim 29, wherein Ar₁ is a group represented by Formula (I),(J), (K) or (L):

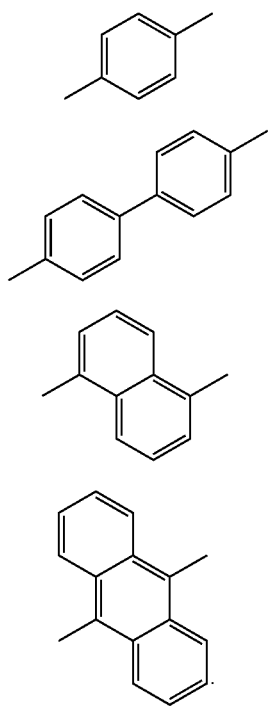

32. A compound according to claim 27, wherein Ar₁ is a group represented by Formula (I), (J), (K) or (L):

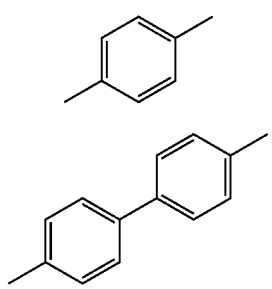

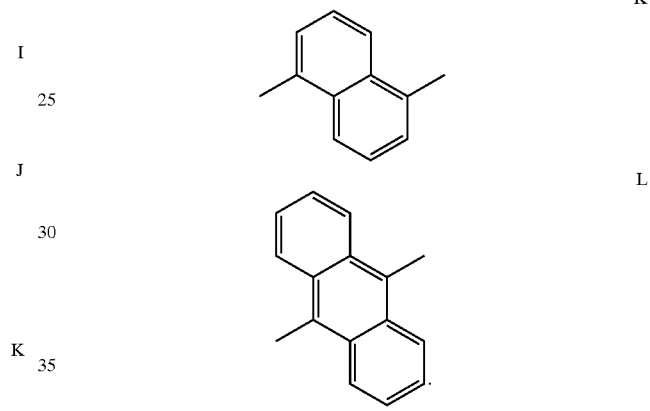

33. The compound of claim 27, wherein Ar₁ is an unsubstituted aromatic hydrocarbon group, a group formed by two identical unsubstituted aromatic hydrocarbon groups directly linked together, an unsubstituted aromatic heterocyclic group, or a group formed by two identical unsubstituted aromatic heterocyclic groups directly linked together.

34. The compound of claim 27, wherein Ar₁ is an unsubstituted aromatic hydrocarbon group or a group formed by two identical unsubstituted aromatic hydrocarbon groups directly linked together.

35. The compound of claim 34, wherein Ar₁ is an unsubstituted aromatic hydrocarbon group.

36. The compound of claim 35, wherein Ar₁ is phenylene, naphthalenediyl or anthracenediyl.

37. The compound of claim 36, wherein Ar₁ is 1,4-phenylene.

38. The compound of claim 27, wherein Ar₁ is a group formed by two identical unsubstituted aromatic hydrocarbon groups directly linked together.

39. The compound of claim 38, wherein Ar₁ is 4,4'-biphenyldiyl.

40. The compound of claim 27, wherein R1, R2 and R3 each independently represents a H atom, unsubstituted alkyl group, unsubstituted aromatic hydrocarbon group, —NH₂, —NHR₅ or —N(R₆)R₇, wherein R₅, R₆ and R₇ are each independently an alkyl, alkenyl, alkynyl, cycloalkyl, cycloalkenyl, aromatic hydrocarbon group or aromatic heterocyclic group, or R₆ and R₇ together with the attached N atom form a heterocyclic group.

41. The compound of claim 40, wherein R1, R2 and R3 each independently represents a H atom or —N(R₆)R₇ wherein $R_6$ and $R_7$ together with the attached N atom form a heterocyclic group.

42. The compound of claim 41, wherein R1, R2 and R3 each represents a H atom or piperidinyl group.

43. The compound of claim 27, wherein $Ar_1$ is an unsubstituted aromatic hydrocarbon group or two identical unsaturated aromatic hydrocarbon groups directly linked together; R1, R2 and R3 each represents a H atom, or two of R1, R2 and R3 both represent H atoms and the remaining one represents a F atom or CN, unsubstituted alkyl, unsubstituted aromatic hydrocarbon, or substituted or unsubstituted amino group; and R4 represents an unsubstituted alkyl or unsubstituted aromatic hydrocarbon group.

44. The compound of claim 43, wherein $Ar_1$ is an unsubstituted aromatic hydrocarbon group or two identical unsaturated aromatic hydrocarbon groups directly linked together; R1, R2, and R3 represent H atoms, or two of R1, R2 and R3 represent H atoms and the remaining one represents a substituted amino group; and R4 represents an unsubstituted alkyl or unsubstituted aromatic hydrocarbon group.

45. The compound of claim 44, wherein R4 is methyl or phenyl.

46. The compound of claim 45, wherein R4 is phenyl.

47. The compound claim 45, represented by Formula (4), (5), (6), (7), (8), (9), (10) or (11):

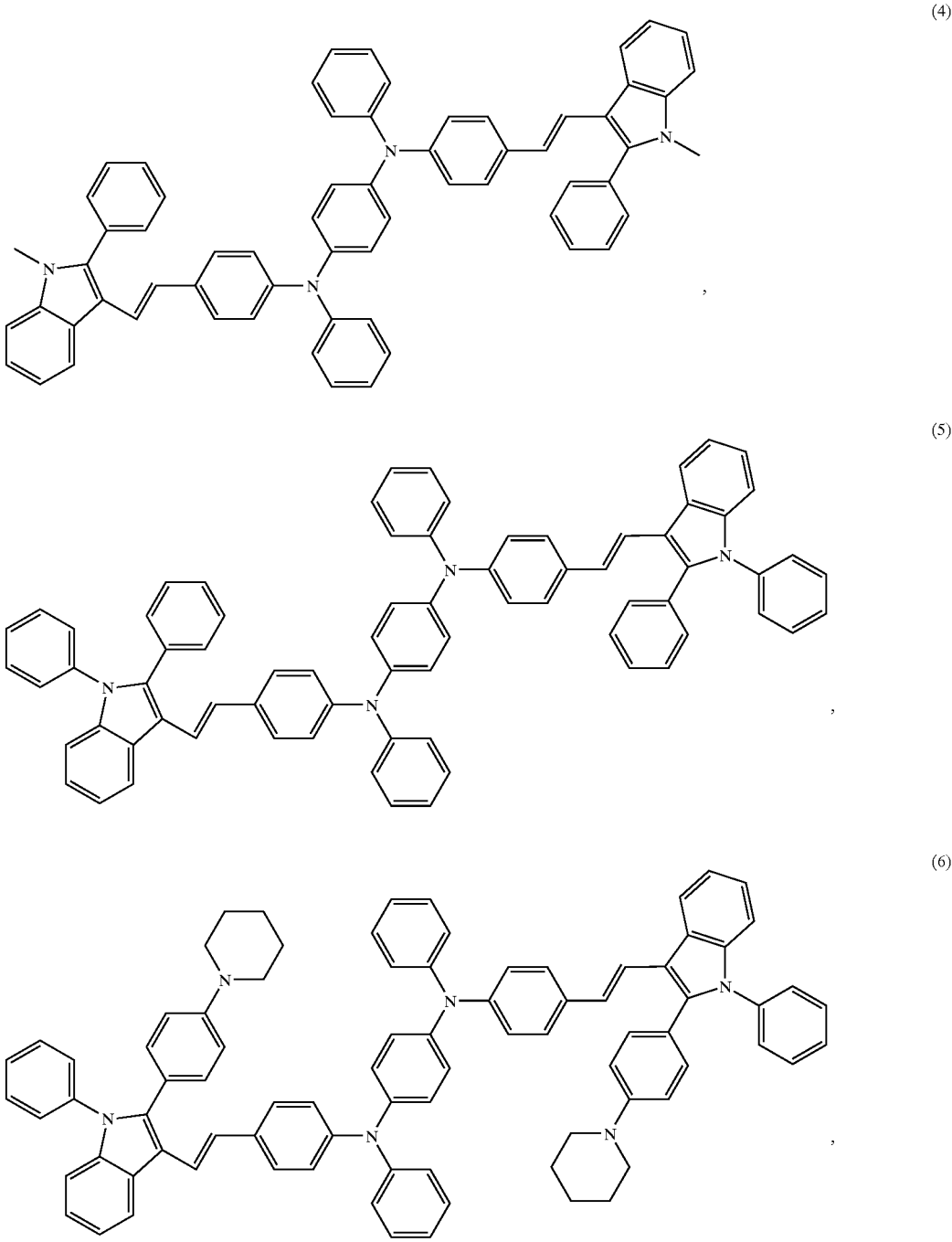

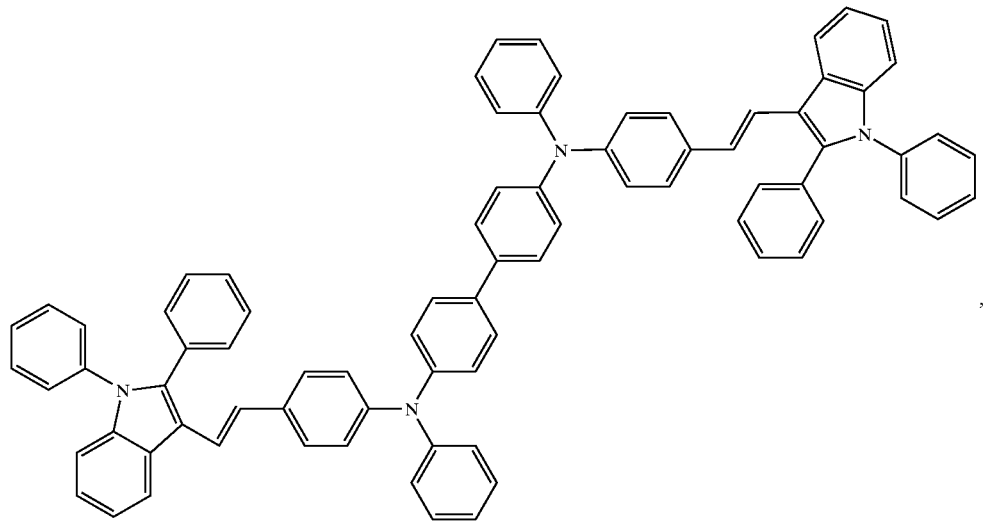
(7)
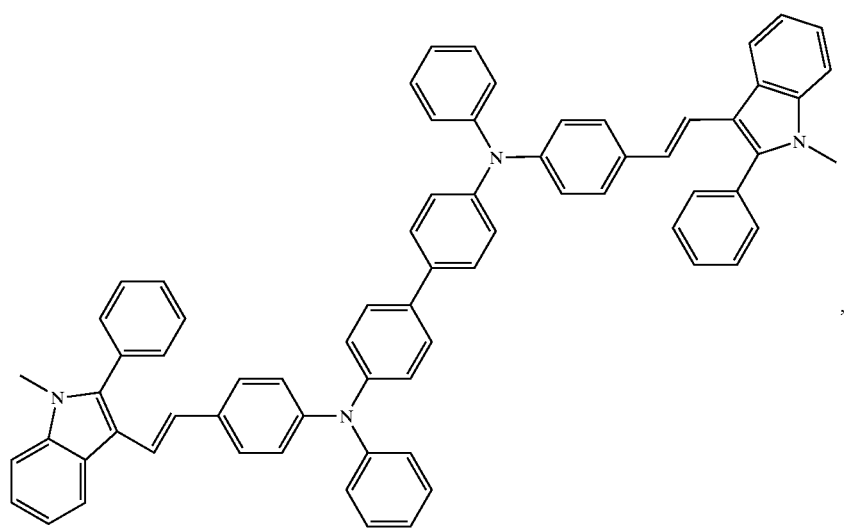
(8)
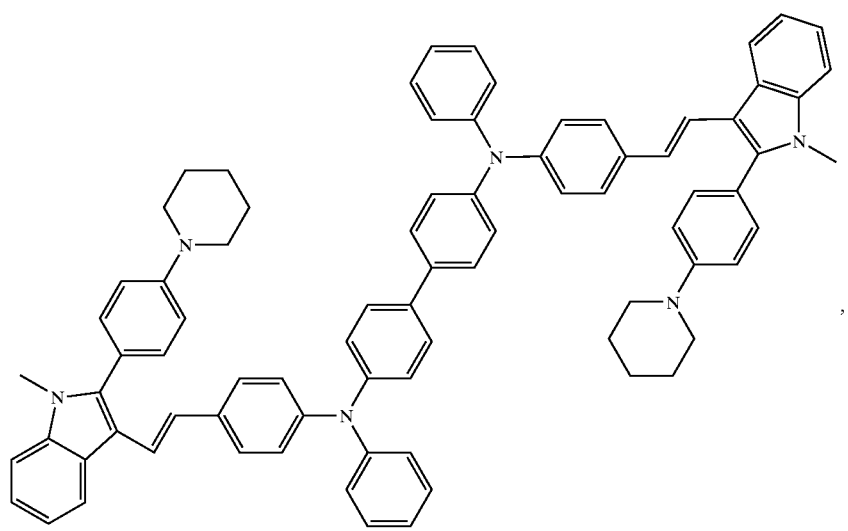
(9)

-continued
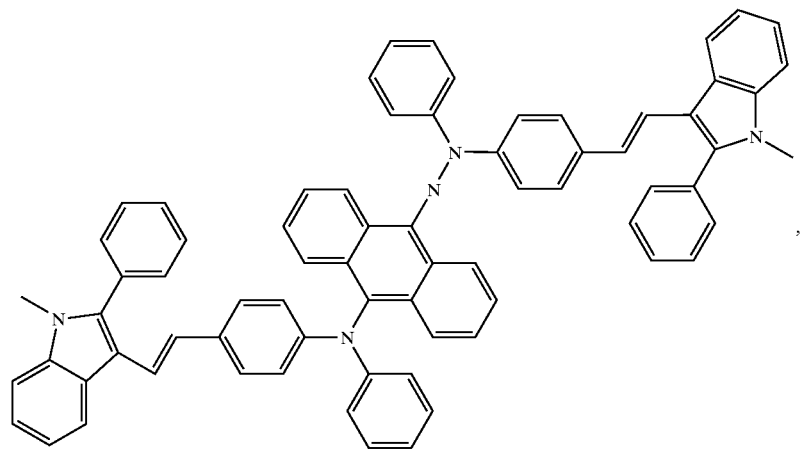
(10)
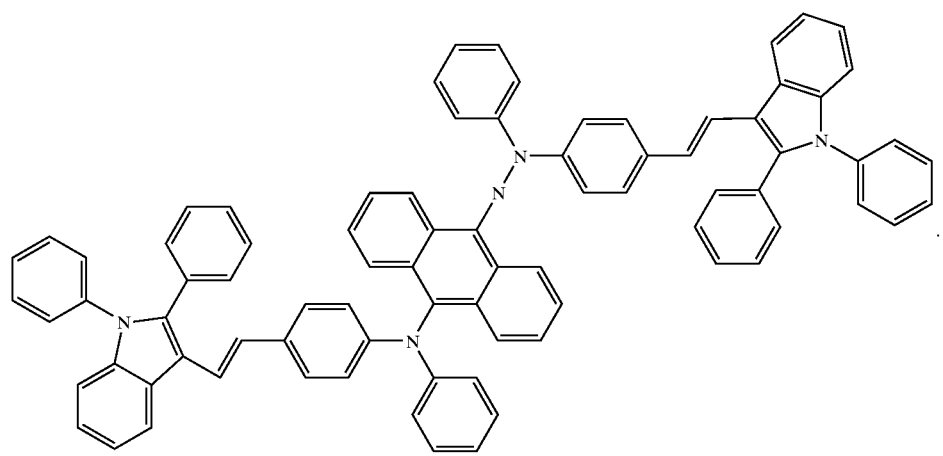
(11)
48. The compound of claim 47, represented by Formula (5) or (7).
* * * * *